(12) United States Patent
Cho et al.

(10) Patent No.: US 11,840,733 B2
(45) Date of Patent: Dec. 12, 2023

(54) METHOD FOR PREDICTING PROGNOSIS OF BREAST CANCER PATIENT

(71) Applicant: GENCURIX INC., Seoul (KR)

(72) Inventors: Sang Rae Cho, Seoul (KR); Young Ho Moon, Seoul (KR); Jin Il Han, Seoul (KR); Young Kee Shin, Seoul (KR)

(73) Assignee: GENCURIX INC., Seoul (KR)

( * ) Notice: Subject to any disclaimer, the term of this patent is extended or adjusted under 35 U.S.C. 154(b) by 1058 days.

(21) Appl. No.: 16/462,655

(22) PCT Filed: Nov. 21, 2017

(86) PCT No.: PCT/KR2017/013272
§ 371 (c)(1),
(2) Date: Nov. 4, 2019

(87) PCT Pub. No.: WO2018/093236
PCT Pub. Date: May 24, 2018

(65) Prior Publication Data
US 2020/0071768 A1 Mar. 5, 2020

(30) Foreign Application Priority Data
Nov. 21, 2016 (KR) .................... 10-2016-0155298

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2005/0260639 A1* | 11/2005 | Nakamura | C12Q 1/6886 435/6.14 |
| 2013/0344482 A1 | 12/2013 | Shin et al. | |
| 2016/0102359 A1* | 4/2016 | Shin | G01N 33/57415 435/6.12 |
| 2016/0168646 A1* | 6/2016 | Peterson | A61K 31/337 435/6.12 |
| 2016/0220687 A1* | 8/2016 | Alhamdan | A61K 38/12 |

FOREIGN PATENT DOCUMENTS

WO    WO 2016-049276    3/2016

OTHER PUBLICATIONS

Cobb et al. (Crit Care Med 2002 vol. 30 p. 2711) (Year: 2002).*
Enard et al. (Science 2002 vol. 296 p. 340) (Year: 2002).*
International Search Report in corresponding PCT Application No. PCT/KR2017/013272, dated Feb. 19, 2018.
Gentles, Andrew J. et al. "The Prognostic Landscape of Genes and Infiltrating Immune Cells across Human Cancers," Nature Medicine, 2015, vol. 21, No. 8, pp. 938-945.
Cheng, Chun-Wen et al., "The clinical implications of MMP-11 and CK-20 Expression in Human Breast Cancer," Clinica Chimica Acta, 2010, vol. 411, No. 3, pp. 234-241.
Kwon, Mi Jeong et al., "Identification of Novel Reference Genes Using Multiplatform Expression Data and Their Validation for Quantitative Gene Expression Analysis," PLoS One, 2009, vol. 4, No. 7, e6162, inner pp. 1-15.

* cited by examiner

*Primary Examiner* — Katherine D Salmon
(74) *Attorney, Agent, or Firm* — LEASON ELLIS LLP

(57) ABSTRACT

The present invention relates to a method for predicting the prognosis of a breast cancer patient. More specifically, to provide information needed to predict the prognosis of a breast cancer patient, the method for predicting the prognosis of breast cancer including the following steps of the present invention comprises: (a) obtaining a biological sample from a breast cancer patient; (b) measuring the mRNA expression level of matrix metallopeptidase 11 (MMP11) and the mRNA expression level of cluster of differentiation 2 (CD2) from patient information or the sample of step (a); (c) normalizing the gene mRNA expression levels selected and measured in step (b); and (d) predicting the prognosis of breast cancer by combining the gene expression levels normalized in step (c), wherein overexpression of the MMP11 indicates a bad prognosis, and overexpression of CD2 indicates a good prognosis.

The method of the present invention has an effect of being capable of more accurately predicting the future prognosis of metastasis, recurrence, or metastatic recurrence in breast cancer patients, and in particular, has a very excellent ability to predict the prognosis of HER2-type breast cancer, the prognosis of which is very poor, and thus can be usefully used to provide clues for the direction of future treatment of breast cancer.

5 Claims, 2 Drawing Sheets
Specification includes a Sequence Listing.

SEQUENCE LISTING

<160> NUMBER OF SEQ ID NOS: 57

<210> SEQ ID NO 1
<211> LENGTH: 22
<212> TYPE: DNA
<213> ORGANISM: Artificial Sequence
<220> FEATURE:
<223> OTHER INFORMATION: Human AURKA primer forward

<400> SEQUENCE: 1
cagggctgcc atataacctg ac                                              22

<210> SEQ ID NO 2
<211> LENGTH: 21
<212> TYPE: DNA
<213> ORGANISM: Artificial Sequence
<220> FEATURE:
<223> OTHER INFORMATION: Human AURKA primer reverse

<400> SEQUENCE: 2
cacctgctga gtaaaacaaa t                                               21

<210> SEQ ID NO 3
<211> LENGTH: 20
<212> TYPE: DNA
<213> ORGANISM: Artificial Sequence
<220> FEATURE:
<223> OTHER INFORMATION: Human CCNB2 primer forward

```
<400> SEQUENCE: 3
ttgggagaac cctcagctct                                              20

<210> SEQ ID NO 4
<211> LENGTH: 20
<212> TYPE: DNA
<213> ORGANISM: Artificial Sequence
<220> FEATURE:
<223> OTHER INFORMATION: Human CCNB2 primer reverse

<400> SEQUENCE: 4
gtttatggac tgcaaaacct                                              20

<210> SEQ ID NO 5
<211> LENGTH: 21
<212> TYPE: DNA
<213> ORGANISM: Artificial Sequence
<220> FEATURE:
<223> OTHER INFORMATION: Human FOXM1 primer forward

<400> SEQUENCE: 5
aagcacattg ccaagccagg c                                            21

<210> SEQ ID NO 6
<211> LENGTH: 19
<212> TYPE: DNA
<213> ORGANISM: Artificial Sequence
<220> FEATURE:
<223> OTHER INFORMATION: Human FOXM1 primer reverse

<400> SEQUENCE: 6
cagggaaagg ttgtggcgg                                               19

<210> SEQ ID NO 7
<211> LENGTH: 21
<212> TYPE: DNA
<213> ORGANISM: Artificial Sequence
<220> FEATURE:
<223> OTHER INFORMATION: Human MKI67 primer forward

<400> SEQUENCE: 7
cagaatgaga gctcccagcc t                                            21

<210> SEQ ID NO 8
<211> LENGTH: 21
<212> TYPE: DNA
<213> ORGANISM: Artificial Sequence
<220> FEATURE:
<223> OTHER INFORMATION: Human MKI67 primer reverse

<400> SEQUENCE: 8
tgcatgagaa ccttcgcact c                                            21

<210> SEQ ID NO 9
<211> LENGTH: 20
<212> TYPE: DNA
<213> ORGANISM: Artificial Sequence
<220> FEATURE:
<223> OTHER INFORMATION: Human  MMP11 primer forward

<400> SEQUENCE: 9
gacagaagag gttcgtgctt                                              20

<210> SEQ ID NO 10
```

```
<211> LENGTH: 18
<212> TYPE: DNA
<213> ORGANISM: Artificial Sequence
<220> FEATURE:
<223> OTHER INFORMATION: Human  MMP11 primer reverse

<400> SEQUENCE: 10
aactgccatg ggaaccga                                                 18

<210> SEQ ID NO 11
<211> LENGTH: 19
<212> TYPE: DNA
<213> ORGANISM: Artificial Sequence
<220> FEATURE:
<223> OTHER INFORMATION: Human  PTTG1 primer forward

<400> SEQUENCE: 11
caggcacccg tgtggttgc                                                19

<210> SEQ ID NO 12
<211> LENGTH: 21
<212> TYPE: DNA
<213> ORGANISM: Artificial Sequence
<220> FEATURE:
<223> OTHER INFORMATION: Human  PTTG1 primer reverse

<400> SEQUENCE: 12
atctaaggct ttgattgaag g                                             21

<210> SEQ ID NO 13
<211> LENGTH: 20
<212> TYPE: DNA
<213> ORGANISM: Artificial Sequence
<220> FEATURE:
<223> OTHER INFORMATION: Human  RACGAP1 primer forward

<400> SEQUENCE: 13
gctgccatgt accaagctgt                                               20

<210> SEQ ID NO 14
<211> LENGTH: 21
<212> TYPE: DNA
<213> ORGANISM: Artificial Sequence
<220> FEATURE:
<223> OTHER INFORMATION: Human  RACGAP1 primer reverse

<400> SEQUENCE: 14
tctctgcaag tgaatcatga g                                             21

<210> SEQ ID NO 15
<211> LENGTH: 18
<212> TYPE: DNA
<213> ORGANISM: Artificial Sequence
<220> FEATURE:
<223> OTHER INFORMATION: Human  RRM2 primer forward

<400> SEQUENCE: 15
tgggaatccc tgaaaccc                                                 18

<210> SEQ ID NO 16
<211> LENGTH: 20
<212> TYPE: DNA
<213> ORGANISM: Artificial Sequence
<220> FEATURE:
<223> OTHER INFORMATION: Human  RRM2 primer reverse

<400> SEQUENCE: 16
```
gaacttcttg gctaaatcgc                                              20

<210> SEQ ID NO 17
<211> LENGTH: 24
<212> TYPE: DNA
<213> ORGANISM: Artificial Sequence
<220> FEATURE:
<223> OTHER INFORMATION: Human TOP2A primer forward

<400> SEQUENCE: 17
aagagtcatt ccacgaataa ccat                                         24

<210> SEQ ID NO 18
<211> LENGTH: 20
<212> TYPE: DNA
<213> ORGANISM: Artificial Sequence
<220> FEATURE:
<223> OTHER INFORMATION: Human TOP2A primer reverse

<400> SEQUENCE: 18
gagggcttcc ttcagtattt                                              20

<210> SEQ ID NO 19
<211> LENGTH: 19
<212> TYPE: DNA
<213> ORGANISM: Artificial Sequence
<220> FEATURE:
<223> OTHER INFORMATION: Human UBE2C primer forward

<400> SEQUENCE: 19
aaaaggctac agcaggagc                                               19

<210> SEQ ID NO 20
<211> LENGTH: 19
<212> TYPE: DNA
<213> ORGANISM: Artificial Sequence
<220> FEATURE:
<223> OTHER INFORMATION: Human UBE2C primer reverse

<400> SEQUENCE: 20
agctgctcca tggatggtc                                               19

<210> SEQ ID NO 21
<211> LENGTH: 18
<212> TYPE: DNA
<213> ORGANISM: Artificial Sequence
<220> FEATURE:
<223> OTHER INFORMATION: Human BTN3A2 primer forward

<400> SEQUENCE: 21
cttcaagcct ggtgagga                                                18

<210> SEQ ID NO 22
<211> LENGTH: 21
<212> TYPE: DNA
<213> ORGANISM: Artificial Sequence
<220> FEATURE:
<223> OTHER INFORMATION: Human BTN3A2 primer reverse

<400> SEQUENCE: 22
ttttctgcag tctatttttc c                                            21

<210> SEQ ID NO 23
<211> LENGTH: 23
<212> TYPE: DNA

```
<213> ORGANISM: Artificial Sequence
<220> FEATURE:
<223> OTHER INFORMATION: Human CCL19 primer forward

<400> SEQUENCE: 23
acttccacta ccttctcatc aag                                          23

<210> SEQ ID NO 24
<211> LENGTH: 19
<212> TYPE: DNA
<213> ORGANISM: Artificial Sequence
<220> FEATURE:
<223> OTHER INFORMATION: Human CCL19 primer reverse

<400> SEQUENCE: 24
ggcggcccct cagtgtggt                                               19

<210> SEQ ID NO 25
<211> LENGTH: 20
<212> TYPE: DNA
<213> ORGANISM: Artificial Sequence
<220> FEATURE:
<223> OTHER INFORMATION: Human CD2 primer forward

<400> SEQUENCE: 25
actgctcgtt ttctatatca                                              20

<210> SEQ ID NO 26
<211> LENGTH: 20
<212> TYPE: DNA
<213> ORGANISM: Artificial Sequence
<220> FEATURE:
<223> OTHER INFORMATION: Human CD2 primer reverse

<400> SEQUENCE: 26
tccagctcct catcatttct                                              20

<210> SEQ ID NO 27
<211> LENGTH: 22
<212> TYPE: DNA
<213> ORGANISM: Artificial Sequence
<220> FEATURE:
<223> OTHER INFORMATION: Human CD52 primer forward

<400> SEQUENCE: 27
tcctcctact caccatcagc ct                                           22

<210> SEQ ID NO 28
<211> LENGTH: 20
<212> TYPE: DNA
<213> ORGANISM: Artificial Sequence
<220> FEATURE:
<223> OTHER INFORMATION: Human CD52 primer reverse

<400> SEQUENCE: 28
tcgttttgtc ctgagagtcc                                              20

<210> SEQ ID NO 29
<211> LENGTH: 23
<212> TYPE: DNA
<213> ORGANISM: Artificial Sequence
<220> FEATURE:
<223> OTHER INFORMATION: Human HLA-DPA1 primer forward

<400> SEQUENCE: 29
ggaccctgtg aaatactgta aag                                          23
```

<210> SEQ ID NO 30
<211> LENGTH: 20
<212> TYPE: DNA
<213> ORGANISM: Artificial Sequence
<220> FEATURE:
<223> OTHER INFORMATION: Human HLA-DPA1 primer reverse

<400> SEQUENCE: 30
cagctggagt tcagatctct                                         20

<210> SEQ ID NO 31
<211> LENGTH: 19
<212> TYPE: DNA
<213> ORGANISM: Artificial Sequence
<220> FEATURE:
<223> OTHER INFORMATION: Human TRBC1 primer forward

<400> SEQUENCE: 31
cagcaagggg tcctgtctg                                          19

<210> SEQ ID NO 32
<211> LENGTH: 21
<212> TYPE: DNA
<213> ORGANISM: Artificial Sequence
<220> FEATURE:
<223> OTHER INFORMATION: Human TRBC1 primer reverse

<400> SEQUENCE: 32
aagagaaagg atttctgaag g                                       21

<210> SEQ ID NO 33
<211> LENGTH: 17
<212> TYPE: DNA
<213> ORGANISM: Artificial Sequence
<220> FEATURE:
<223> OTHER INFORMATION: Human CTBP1 primer forward

<400> SEQUENCE: 33
ccttgggcat catcgga                                            17

<210> SEQ ID NO 34
<211> LENGTH: 18
<212> TYPE: DNA
<213> ORGANISM: Artificial Sequence
<220> FEATURE:
<223> OTHER INFORMATION: Human CTBP1 primer reverse

<400> SEQUENCE: 34
gttgaagccg aaggcctt                                           18

<210> SEQ ID NO 35
<211> LENGTH: 22
<212> TYPE: DNA
<213> ORGANISM: Artificial Sequence
<220> FEATURE:
<223> OTHER INFORMATION: Human CUL1 primer forward

<400> SEQUENCE: 35
agtactgaat tcttgcagca ga                                      22

<210> SEQ ID NO 36
<211> LENGTH: 23
<212> TYPE: DNA
<213> ORGANISM: Artificial Sequence
<220> FEATURE:

<223> OTHER INFORMATION: Human CUL1 primer reverse

<400> SEQUENCE: 36
tcttcgttgt tcctcaagca gac                                           23

<210> SEQ ID NO 37
<211> LENGTH: 22
<212> TYPE: DNA
<213> ORGANISM: Artificial Sequence
<220> FEATURE:
<223> OTHER INFORMATION: Human UBQLN1 primer forward

<400> SEQUENCE: 37
gaaatcctca gcttcaagaa ca                                            22

<210> SEQ ID NO 38
<211> LENGTH: 22
<212> TYPE: DNA
<213> ORGANISM: Artificial Sequence
<220> FEATURE:
<223> OTHER INFORMATION: Human UBQLN1 primer reverse

<400> SEQUENCE: 38
tgacattgct gatagtgtat ca                                            22

<210> SEQ ID NO 39
<211> LENGTH: 8
<212> TYPE: DNA
<213> ORGANISM: Artificial Sequence
<220> FEATURE:
<223> OTHER INFORMATION: Human AURKA probe

<400> SEQUENCE: 39 gctgccct                                                             8

<210> SEQ ID NO 40
<211> LENGTH: 8
<212> TYPE: DNA
<213> ORGANISM: Artificial Sequence
<220> FEATURE:
<223> OTHER INFORMATION: Human CCNB2 probe

<400> SEQUENCE: 40 ctcaggca                                                             8

<210> SEQ ID NO 41
<211> LENGTH: 8
<212> TYPE: DNA
<213> ORGANISM: Artificial Sequence
<220> FEATURE:
<223> OTHER INFORMATION: Human FOXM1 probe

<400> SEQUENCE: 41 aggctgga                                                             8

<210> SEQ ID NO 42
<211> LENGTH: 8
<212> TYPE: DNA
<213> ORGANISM: Artificial Sequence
<220> FEATURE:
<223> OTHER INFORMATION: Human MKI67 probe

<400> SEQUENCE: 42 gaggagag                                                             8

```
<210> SEQ ID NO 43
<211> LENGTH: 8
<212> TYPE: DNA
<213> ORGANISM: Artificial Sequence
<220> FEATURE:
<223> OTHER INFORMATION: Human MMP11 probe

<400> SEQUENCE: 43 cgctggga                                                                  8

<210> SEQ ID NO 44
<211> LENGTH: 8
<212> TYPE: DNA
<213> ORGANISM: Artificial Sequence
<220> FEATURE:
<223> OTHER INFORMATION: Human PTTG1 probe

<400> SEQUENCE: 44 ctgaagct                                                                  8

<210> SEQ ID NO 45
<211> LENGTH: 8
<212> TYPE: DNA
<213> ORGANISM: Artificial Sequence
<220> FEATURE:
<223> OTHER INFORMATION: Human RACGAP1 probe

<400> SEQUENCE: 45 gccccagg                                                                  8

<210> SEQ ID NO 46
<211> LENGTH: 7
<212> TYPE: DNA
<213> ORGANISM: Artificial Sequence
<220> FEATURE:
<223> OTHER INFORMATION: Human RRM2 probe

<400> SEQUENCE: 46 aaagcca                                                                   7

<210> SEQ ID NO 47
<211> LENGTH: 8
<212> TYPE: DNA
<213> ORGANISM: Artificial Sequence
<220> FEATURE:
<223> OTHER INFORMATION: Human TOP2A probe

<400> SEQUENCE: 47 gcctctga                                                                  8

<210> SEQ ID NO 48
<211> LENGTH: 8
<212> TYPE: DNA
<213> ORGANISM: Artificial Sequence
<220> FEATURE:
<223> OTHER INFORMATION: Human UBE2C probe

<400> SEQUENCE: 48 gggaaggc                                                                  8

<210> SEQ ID NO 49
<211> LENGTH: 8
<212> TYPE: DNA
<213> ORGANISM: Artificial Sequence
<220> FEATURE:
<223> OTHER INFORMATION: Human BTN3A2 probe
```

```
<400> SEQUENCE: 49 caaggtgg                                                              8

<210> SEQ ID NO 50
<211> LENGTH: 8
<212> TYPE: DNA
<213> ORGANISM: Artificial Sequence
<220> FEATURE:
<223> OTHER INFORMATION: Human CCL19 probe

<400> SEQUENCE: 50 gtgcctgc                                                              8

<210> SEQ ID NO 51
<211> LENGTH: 8
<212> TYPE: DNA
<213> ORGANISM: Artificial Sequence
<220> FEATURE:
<223> OTHER INFORMATION: Human CD2 probe

<400> SEQUENCE: 51 gaggagtc                                                              8

<210> SEQ ID NO 52
<211> LENGTH: 8
<212> TYPE: DNA
<213> ORGANISM: Artificial Sequence
<220> FEATURE:
<223> OTHER INFORMATION: Human CD52 probe

<400> SEQUENCE: 52 tcctggtt                                                              8

<210> SEQ ID NO 53
<211> LENGTH: 23
<212> TYPE: DNA
<213> ORGANISM: Artificial Sequence
<220> FEATURE:
<223> OTHER INFORMATION: Human HLA-DPA1 probe

<400> SEQUENCE: 53
ggaccctgtg aaatactgta aag                                            23

<210> SEQ ID NO 54
<211> LENGTH: 9
<212> TYPE: DNA
<213> ORGANISM: Artificial Sequence
<220> FEATURE:
<223> OTHER INFORMATION: Human TRBC1 probe

<400> SEQUENCE: 54 tggcagaca                                                             9

<210> SEQ ID NO 55
<211> LENGTH: 8
<212> TYPE: DNA
<213> ORGANISM: Artificial Sequence
<220> FEATURE:
<223> OTHER INFORMATION: Human CTBP1 probe

<400> SEQUENCE: 55 gccccacg                                                              8

<210> SEQ ID NO 56
<211> LENGTH: 8
```

```
<212> TYPE: DNA
<213> ORGANISM: Artificial Sequence
<220> FEATURE:
<223> OTHER INFORMATION: Human CUL1 probe

<400> SEQUENCE: 56 gcagaggc                                                                  8

<210> SEQ ID NO 57
<211> LENGTH: 8
<212> TYPE: DNA
<213> ORGANISM: Artificial Sequence
<220> FEATURE:
<223> OTHER INFORMATION: Human UBQLN1 probe

<400> SEQUENCE: 57 ttgggagc                                                                  8
```

METHOD FOR PREDICTING PROGNOSIS OF BREAST CANCER PATIENT

CROSS-REFERENCE TO RELATED PATENT APPLICATIONS

This application is a U.S. National Phase Application under 35 U.S.C. § 371 of International Patent Application No. PCT/KR2017/013272, filed Nov. 21, 2017, and claims priority to KR 10-2016-0155298, filed Nov. 21, 2016, all of which are incorporated by reference in their entireties. The International Application was published on May 24, 2018 as International Publication No. WO 2018/093236 A2.

SEQUENCE LISTING

The instant application contains a Sequence Listing which has been submitted electronically in ASCII format and is hereby incorporated by reference in its entirety. Said ASCII copy, created on May 21, 2019, is named 10524_007868-US0_ST25.txt and is 11.5 kilobytes in size.

TECHNICAL FIELD

This application claims priority from Korean Patent Application No. 10-2016-0155298, filed on Nov. 21, 2016, the entire contents of which are incorporated herein by reference.

The present invention relates to a method for predicting the prognosis of a breast cancer patient. More specifically, to provide information needed to predict the prognosis of a breast cancer patient, the method for predicting the prognosis of breast cancer including the following steps of the present invention comprises: (a) measuring mRNA expression levels of MMP11 (matrix metallopeptidase 11) and CD2 (cluster of differentiation 2) from a biological sample or an information of the breast cancer patient; (b) normalizing the mRNA expression levels of the genes selected and measured in the step (a); and (c) predicting the prognosis of breast cancer by combining the normalized expression levels of the genes in step (b), wherein the prognosis is predicted to be poor when the MMP11 is over-expressed and the prognosis is predicted to be good when the CD2 is over-expressed.

BACKGROUND OF THE INVENTION

Breast cancer is a significant adventitious disease and can be classified as Luminal A, Luminal B, HER2, and Triple Negative Breast Cancer (TNBC), depending on the expression status of hormone receptors including estrogen receptor (ER) or progesterone receptor (PR) and human epidermal growth factor receptor 2 (HER2). Each breast cancer subtype has distinctive molecular features, and each subtype shows a different prognosis. In other words, Luminal A type has the best prognosis and HER2 and TNBC subtypes have the worst prognosis. Since the treatment of breast cancer depends on the molecular subtype and the prognosis of the patient, it is very important to select a specific biomarker for predicting the prognosis, which corresponds to each molecular subtype, in order to establish an appropriate treatment method.

Gene expression-based approaches provide valuable information for predicting the prognosis, and commercial assays based on complex gene expression profiling techniques using frozen or formalin fixed paraffin embedded (FFPE) samples have been developed for ER-positive breast cancer. However, the assays based on proliferation-related genes and using pattern of complex gene expression have some limitations. In addition, commercial kits based on various complex gene predictors of clinical outcome can only predict prognosis for hormone receptor-positive breast cancer subtypes. There is no commercial kit for hormone receptor negative breast cancer subtypes.

Meta-analysis of publicly available microarray data from more than 2,100 patients shows that the important physiological processes associated with clinical outcomes in breast cancer patients are dependent on the molecular subtype of breast cancer (Clinical cancer research: an official journal of the American Association for Cancer Research 14 (16):5158-5165). In this study, seven prototype genes representing different physiological processes (proliferation, tumor invasion/metastasis, immune response, angiogenesis, apoptosis phenotype, ER and HER2 signaling) were selected (AURKA, PLAU, STAT1, VEGF, CASP3, ESR1, and ERBB2), and these seven genes were evaluated with the clinical parameters of each patient with breast cancer subtype and the non-recurrence-free survival period. As a result, there are limitations that the proliferation-related genes showed the predictive possibility of prognosis only for the ER+/HER2− subtypes, and the genes involved in tumor invasion, immune response, etc., showed the predictive possibility of prognosis only for ER−/HER2− or ER−/HER2+ subtypes.

In a recent study reporting characteristics of genes that predict remote metastasis in genes for predicting the prognosis or recurrence or hormone receptor-negative (HR−) breast cancer, the genes associated with the immune response are additionally reported to be associated mainly with good clinical outcomes in patients with HR-breast cancer (Breast Cancer Res 12 (5):R85. doi:10.1186/bcr2753, Genome biology 8 (8):R157. doi:gb-2007-8-8-r157 [pii], Breast Cancer Res 10 (4):R73. doi:10.1186/bcr2138). However, these results are mainly based on gene expression microarray data, and most of these genes or genetic characteristics for predicting the prognosis require further validation.

Therefore, it is necessary to establish more accurate factors and models for predicting the prognosis in order to more accurately predict the prognosis according to the molecular subtype of breast cancer and to wisely select appropriate treatment method at present.

DETAILED DESCRIPTION OF THE INVENTION

Technical Problem

Accordingly, the present inventors evaluated the expression of 16 candidate genes for predicting the prognosis in large quantities of FFPE tissue samples using quantitative real-time reverse transcription polymerase chain reaction (qRT-PCR). And, the evaluated 16 candidate genes were analyzed with conventional clinicopathologic factors and the risk of distant metastasis of 819 breast cancer patients who were classified according to molecular subtypes. As a result, genetic or clinicopathologic factors were selected to predict the risk of distant metastasis according to breast cancer molecular subtype based on significant factors for predicting the prognosis, and thus, the present invention has been completed by developing a model for predicting the prognosis of the distant metastasis of breast cancer patients.

Accordingly, an aspect of the present invention is directed to provide a method for predicting the prognosis of breast cancer to provide information necessary for predicting the prognosis of a breast cancer patient, the method comprising the steps of:
- (a) measuring mRNA expression levels of MMP11 (matrix metallopeptidase 11) and CD2 (cluster of differentiation 2) from a biological sample or an information of the breast cancer patient;
- (b) normalizing the mRNA expression levels of the genes selected and measured in the step (a); and
- (c) predicting the prognosis of breast cancer by combining the normalized expression levels of the genes, wherein the prognosis is predicted to be poor when the MMP11 is over-expressed and the prognosis is predicted to be good when the CD2 is over-expressed.

Another aspect of the present invention is to provide a method for predicting the prognosis of breast cancer to provide information necessary for predicting the prognosis of a breast cancer patient, the method comprising the steps of:
- (a) measuring mRNA expression levels of MMP11 (matrix metallopeptidase 11) and CD2 (cluster of differentiation 2) genes for the prediction of prognosis and those of CTBP1 (C-terminal-binding protein 1), CUL1 (cullin 1), and UBQLN1 (Ubiquilin-1) genes for normalization from a biological sample of the breast cancer patient;
- (b) normalizing ($\Delta C_q$) the expression levels of the (target) genes for predicting the prognosis by putting the mRNA expression levels of the target gene for the prediction of prognosis and the genes for normalization measured in the step (a) into the following Equations 1:

$$\Delta Cq\_\text{target} = ((Cq\_\text{CTBP1} + Cq\_\text{CUL1} + Cq\_\text{UBQLN1})/3) - Cq\_\text{target} + 30; \qquad \text{<Equation 1>}$$

- (c) calculating a risk score by putting a normalized value obtained in the step (b) into the following Equation 2:

$$\text{Risk score} = a \times \Delta Cq\_\text{MMP11} + b \times \Delta Cq\_\text{CD2} \qquad \text{<Equation 2>}$$

(wherein, a is from 0.15 to 0.76, and b is from −0.81 to −0.15); and
- (d) predicting that the greater the score calculated in the step (c) is, the poorer the prognosis is.

Another aspect of the present invention is to provide a composition for predicting the prognosis of a breast cancer patient, the composition comprising agents for measuring the expression levels of MMP11 and CD2 genes, respectively.

Another aspect of the present invention is to provide a composition for predicting the prognosis of a breast cancer patient, the composition consisting of agents for measuring the expression levels of MMP11 and CD2 genes, respectively.

Still another aspect of the present invention is to provide a composition for predicting the prognosis of a breast cancer patient, the composition essentially consisting of agents for measuring the expression levels of MMP11 and CD2 genes, respectively.

Still another aspect of the present invention is to provide a kit for predicting the prognosis of a breast cancer patient, the kit comprising agents for measuring the expression levels of MMP11 and CD2 genes, respectively.

Still another aspect of the present invention is to provide a use of agents for measuring the expression levels of MMP11 and CD2 genes for preparing agents for predicting the prognosis of a breast cancer patient.

Technical Solution

An embodiment according to an aspect of the present invention provides a method for predicting the prognosis of breast cancer to provide information necessary for predicting the prognosis of a breast cancer patient, the method comprising the steps of:

The method for predicting the prognosis of breast cancer to provide information necessary for predicting the prognosis of a breast cancer patient, the method comprising the steps of:
- (a) measuring mRNA expression levels of MMP11 (matrix metallopeptidase 11) and CD2 (cluster of differentiation 2) from a biological sample or an information of the breast cancer patient;
- (b) normalizing the mRNA expression levels of the genes selected and measured in the step (a); and
- (c) predicting the prognosis of breast cancer by combining the normalized expression levels of the genes, wherein the prognosis is predicted to be poor when the MMP11 is over-expressed and the prognosis is predicted to be good when the CD2 is over-expressed.

Another embodiment according to an aspect of the present invention provides a method for predicting the prognosis of breast cancer to provide information necessary for predicting the prognosis of a breast cancer patient, the method comprising the steps of:
- (a) measuring mRNA expression levels of MMP11 (matrix metallopeptidase 11) and CD2 (cluster of differentiation 2) genes for the prediction of prognosis and those of CTBP1 (C-terminal-binding protein 1), CUL1 (cullin 1), and UBQLN1 (Ubiquilin-1) genes for normalization from a biological sample of the breast cancer patient;
- (b) normalizing ($\Delta C_q$) the expression levels of the (target) genes for predicting the prognosis by putting the mRNA expression levels of the target gene for the prediction of prognosis and the genes for normalization measured in the step (a) into the following Equations 1:

$$\Delta Cq\_\text{target} = ((Cq\_\text{CTBP1} + Cq\_\text{CUL1} + Cq\_\text{UBQLN1})/3) - Cq\_\text{target} + 30; \qquad \text{<Equation 1>}$$

- (c) calculating a risk score by putting a normalized value obtained in the step (b) into the following Equation 2:

$$\text{Risk score} = a \times \Delta Cq\_\text{MMP11} + b \times \Delta Cq\_\text{CD2} \qquad \text{<Equation 2>}$$

(wherein, a is from 0.15 to 0.76, and b is from −0.81 to −0.15); and
- (d) predicting that the greater the score calculated in the step (c) is, the poorer the prognosis is.

Another embodiment according to an aspect of the present invention provides a composition for predicting the prognosis of a breast cancer patient, the composition comprising agents for measuring the expression levels of MMP11 and CD2 genes, respectively.

Another embodiment according to an aspect of the present invention provides a composition for predicting the prognosis of a breast cancer patient, the composition consisting of agents for measuring the expression level of MMP11 and CD2 genes, respectively.

Another embodiment according to an aspect of the present invention provides a composition for predicting the prognosis of a breast cancer patient, the composition essentially consisting of agents for measuring the expression level of MMP11 and CD2 genes, respectively.

Another embodiment according to an aspect of the present invention provides a kit for predicting the prognosis of a breast cancer patient, the kit comprising agents for measuring the expression levels of MMP11 and CD2 genes, respectively.

An embodiment according to another aspect of the present invention provides a use of agents for measuring the expression levels of MMP11 and CD2 genes for preparing agents for predicting the prognosis of a breast cancer patient.

Hereinafter, the present invention will be described in detail.

The present invention provides a method for predicting the prognosis of breast cancer to provide information necessary for predicting the prognosis of a breast cancer patient, the method comprising the steps of:
(a) measuring mRNA expression levels of MMP11 (matrix metallopeptidase 11) and CD2 (cluster of differentiation 2) from a biological sample or an information of the breast cancer patient;
(b) normalizing the mRNA expression levels of the genes selected and measured in the step (a); and
(c) predicting the prognosis of breast cancer by combining the normalized expression levels of the genes, wherein the prognosis is predicted to be poor when the MMP11 is over-expressed and the prognosis is predicted to be good when the CD2 is over-expressed.

The term "prognosis" in the present invention means progression of the disease during or after the treatment of breast cancer, preferably means progression of disease after treatment, and comprises overall survival, disease free survival or distant metastasis free survival, but is not limited thereto. The term "disease progression" as used herein refers to a concept including cancer cure, recurrence, metastasis or metastatic recurrence, and more preferably refers to metastatic recurrence but is not limited thereto. The prognosis (or diagnosis of prognosis) of metastatic recurrence among these can provide clues to the direction of breast cancer treatment, especially because it can be used to determine in advance whether the tumor in the early stage breast cancer patient can develop into metastatic breast cancer in the future. This is a very meaningful task.

The "metastatic recurrence" in the present invention is a concept comprising local metastatic recurrence that occurs in breast cancer site before treatment and/or the ipsilateral breast and/or the contralateral breast, and the distant metastatic recurrence that occurs in distant areas such as the lung, liver, bone, lymph nodes, skin, and brain. Preferably, in the present invention, the metastatic recurrence may be distant metastatic recurrence.

The term "metastatic recurrence" in the present invention means, after the initial treatment, that cancer cells derived and modified from at least one breast tumor continue to grow to be cancer at the site remote from the tumor (hereinafter referred to as "distant area"). The distant area may be, for example, in one or more lymph nodes, which may be mobile or fixed, ipsilateral or contralateral to the tumor, and be the collarbone or underarm.

The prediction of the prognosis of breast cancer is mainly determined by the stage of disease after surgery to evaluate the size of the tumor (T), the metastasis to the periphery of the lymph nodes (N), and the distant metastasis (M) (TNM staging). The prediction of the prognosis in patients classified according to TNM stage is also different even in the same stage. Thus, the prediction of the prognosis in breast cancer of the same stage can be determined by expression of estrogen or progesterone receptor (ER or PR) and overexpression of HER2 (human epidermal growth factor receptor 2) or amplification of the gene. Even breast cancer of the same stage, the pathology and prognosis vary significantly depending on the expression of estrogen receptor, progesterone receptor or HER2, so it is necessary to clearly distinguish it and to set the treatment method specifically.

Therefore, recently, the characteristics of breast cancer were classified by gene and molecular biology (Table 1). According to the subtype, the outcome and prognosis of treatment are different, and it is used as an index for selection of surgical method or chemotherapy.

TABLE 1

| Molecular biological subtype classification of breast cancer | | |
|---|---|---|
| Subtype | Characterization | Frequency (%) |
| Luminal A type | ER positive and/or PR positive HER2 negative Low expression of Ki67 | 30~70 |
| Luminal B type | ER positive and/or PR positive HER2 positive (or high expression of Ki6 and HER2 negative) | 10~20 |
| Triple negative type | ER negative PR negative HER2 negative | 15~20 |
| HER2 type | ER negative PR negative HER2 positive | 5~15 |

In the present invention, the breast cancer does not distinguish its molecular subtype, but is preferably a HER2 breast cancer type. In general, breast cancer patients with HER2 overexpression are known to have poor prognosis than those who do not. Therefore, the method for predicting the prognosis of the present invention can be used to predict an accurate prognosis of breast cancer patients of HER2 type and to develop an effective treatment strategy against bad prognosis.

Hereinafter, each step of the method for predicting the prognosis of the breast cancer is described in detail.

(a) Obtaining a Biological Sample from the Breast Cancer Patient;

In the present invention, the biological sample may be a breast cancer tissue of the breast cancer patient. The breast cancer tissue may also contain some normal cells, preferably a formalin-fixed paraffin-embedded (FFPE) tissue, a fresh tissue, and a frozen tissue containing cancer cells of a patient, but is not limited thereto.

(b) Measuring mRNA Expression Levels of MMP11 (Matrix Metallopeptidase 11) and CD2 (Cluster of Differentiation 2) from the Sample or Information or the Patient in the Step (a).

In one example of the present invention, the inventors performed univariate and multivariate analyzes on the expression of 16 candidate genes, typical clinicopathologic factors, and clinical outcome according to the molecular subtypes of breast cancer. As a result, it was confirmed that mRNA expression level of MMP11 or CD2 was significantly associated with the prognosis of breast cancer patients.

In addition, the present invention is characterized by combining factors of predicting the prognosis consisting of mRNA expression level of MMP11 (matrix metallopeptidase 11) and mRNA expression level of CD2 (cluster of differentiation 2) in order to predict the prognosis of breast cancer. Therefore, the combination of mRNA expression levels of MMP11 and CD2 is evaluated to predict the prognosis of breast cancer patients.

Each of the above genes may be a sequence of each gene or a synonym of each gene known in the art, preferably a sequence of each gene derived from a human, more preferably MMP11 (Gene ID: 4320) and CD2 (Gene ID: 914), but is not limited thereto.

Synonyms and sequences for each gene can be found in GenBank.

In the present invention, the mRNA expression level can be measured by any method performed in the art to measure the expression level of the gene. Preferably, the methods can be performed using a microarray, a polymerase chain reaction (PCR), RT-PCR (qRT-PCR), real-time PCR, northern blot, DNA chip and RNA chip, but are not limited thereto.

The measurement of the expression level of the gene of interest of the present invention is preferably a detection of the expression level of the gene of interest, more preferably the quantitative detection of the expression level of the gene of interest. In order to detect the expression level, mRNA isolation in the sample tissue and cDNA synthesis in the mRNA may be necessary. In order to isolate mRNA, a method of isolating RNA in a sample known in the art can be used. Preferably, the sample is an FFPE sample, and thus it may be a method of separating mRNA suitable for FFPE sample. As the cDNA synthesis process, a cDNA synthesis method known in the art using mRNA as a template can be used. Preferably, the expression level of the predictive marker of the effectiveness of chemotherapy in the breast cancer patient of the present invention is quantitative detection of mRNA expression in the FFPE sample. Therefore, it can be measured by the mRNA isolation method for FFPE samples and real time reverse transcription quantitative polymerase chain reaction (RT-qPCR).

In addition, measurement of the expression level of the gene of interest in the present invention can be performed according to a method known in the art, but can be measured by an optical quantitative analysis system using a probe labeled with a reporter fluorescent dye and/or a quencher fluorescent dye. The measurement may be performed by a commercially available equipment, for example, a system such as ABIPRISM 7700™ Sequence Detection System™, Roche Molecular Biochemicals Lightcycler, and software attached thereto. Such measurement data can be expressed as a measurement value or a threshold cycle (Ct or Cp). The point at which the measured fluorescence value is recorded as the first statistically significant point is the threshold cycle. This indicates that the detection target appears in inverse proportion to the initial value existing as a template of the PCR reaction, so that when the value of the threshold cycle is smaller, targets to detect exist more quantitatively.

(c) Normalizing the mRNA Expression Levels of the Genes Selected and Measured in the Step (b);

The expression levels of the genes to be detected in the present invention may be different in expression amounts of overall genes or expression levels depending on the patient or the sample, so the normalization is required. The normalization is accomplished through differences in expression amounts or expression levels of genes that may indicate differences in basal expression amounts or expression levels. Preferably, the expression level of one to three genes (or the average of these expression levels when a plurality of genes are selected) in the group consisting of CTBP1 (C-terminal-binding protein 1), CUL1 (cullin 1) and UBQLN1 (Ubiquilin-1) is measured, and then expressed as a relative expression value of MMP11 and/or CD2 thereof.

(d) Predicting the Prognosis of Breast Cancer by Combining the Normalized Expression Levels of the Genes in the Step (c), Wherein the Prognosis is Predicted to be Poor when the MMP11 is Over-Expressed and the Prognosis is Predicted to be Good when the CD2 is Over-Expressed.

In the present invention, the term "bad prognosis" means a high-risk group having a high probability of cancer metastasis, recurrence or metastatic recurrence after treatment, and a "good prognosis" means a low-risk group having a low probability of metastasis, recurrence or metastatic recurrence. Preferably, a "bad prognosis" refers to a high-risk group with a high probability of metastasis, recurrence or metastatic recurrence of cancer, and a "good prognosis" refers to a low-risk group with a low probability of metastasis, recurrence or metastatic recurrence.

In the present invention, the overexpression of the MMP11 is closely related to the bad prognosis and the overexpression of the CD2 is closely related to the good prognosis in the breast cancer patient. Therefore, the prognosis of breast cancer can be more accurately predicted by combining the expression pattern of the MMP11 and the CD2.

The present invention provides a method for predicting the prognosis of breast cancer to provide information necessary for predicting the prognosis of a breast cancer patient, the method comprising the steps of:

(a) measuring mRNA expression levels of MMP11 (matrix metallopeptidase 11) and CD2 (cluster of differentiation 2) genes for the prediction of prognosis and those of CTBP1 (C-terminal-binding protein 1), CUL1 (cullin 1), and UBQLN1 (Ubiquilin-1) genes for normalization from a biological sample of the breast cancer patient;

(b) normalizing ($\Delta C_q$) the expression levels of the (target) genes for predicting the prognosis by putting the mRNA expression levels of the target gene for the prediction of prognosis and the genes for normalization measured in the step (a) into the following Equations 1:

$$\Delta Cq\_target = ((Cq\_CTBP1 + Cq\_CUL1 + Cq\_UBQLN1)/3) - Cq\_target + 30; \qquad \text{<Equation 1>}$$

(c) calculating a risk score by putting a normalized value obtained in the step (b) into the following Equation 2:

$$\text{Risk score} = a \times \Delta Cq\_MMP11 + b \times \Delta Cq\_CD2 \qquad \text{<Equation 2>}$$

(wherein, a is from 0.15 to 0.76, and b is from −0.81 to −0.15); and (d) predicting that the greater the score calculated in the step (c) is, the poorer the prognosis is.

The (a) and (b) are the same as described above.

(c) normalizing ($\Delta C_q$) the expression level of the gene (target) for predicting the prognosis by putting the mRNA expression level of the target gene for predicting the prognosis and the gene for normalization measured in the step (b) into the following Equations 1

$$\Delta C_q\_target = ((C_q\_CTBP1 + C_q\_CUL1 + C_q\_UBQLN1)/3) - C_q\_target + 30; \qquad \text{<Equation 1>}$$

In the present invention, the Cq values of the MMP11 and CD2 genes represent relative expression levels normalized by expression levels of three reference genes. The relative expression value of each gene is calculated according to the following equation based on the difference between the average Cq value of the three reference genes and the target (MMP11 or CD2) Cq value in each sample.

$$\Delta C_q\_target = ((C_q\_CTBP1 + C_q\_CUL1 + C_q\_UBQLN1)/3) - C_q\_target + 30$$

The term of "Cq" value means the number of cycles when fluorescence measured by amplifying a product of a gene sequence as a target using qPCR reaches a threshold value. Therefore, the Cq value gets the smaller, the product of the target gets the more, and the Cq value is the larger, the product of the target is the less.

(d) calculating a risk score by putting the normalization value in the step (c) into the following Equation 2

$$\text{Risk score} = a \times \Delta C_q\_MMP11 + b \times \Delta C_q\_CD2 \qquad \text{<Equation 2>}$$

(wherein, a is from 0.15 to 076, and b is from −0.81 to −0.15);

According to one example of the present invention, genes with a statistical significance (p<0.05) in the Cox regression analysis were selected as genes related to prognosis among genes involved in immune activation and cell proliferation which are two major biological features that govern the clinical outcome of breast cancer patients. Also, based on the results of the multivariate analysis of each gene, the risk score (the molecular predictive value of the occurrence of distant metastasis within 10 years) was calculated by a combination of the relative expression levels of two genes for predicting prognosis ((MMP11 and CD2) standardized by the average value of expression levels of the three reference genes. The coefficients in each variable were obtained from the Cox model and the risk score was defined as a linear combination of the coefficients to predict the distant metastasis according to the following equation:

$$\text{Risk score} = a \times \Delta C_{q\_}\text{MMP11} + b \times \Delta C_{q\_}\text{CD2}$$

(wherein, a is from 0.15 to 0.76, and the b is from −0.81 to −0.15)

The gene calculates a score of predicting the prognosis through a linear combination of the respective coefficients. The MMP11 has a positive coefficient. The CD2 has a negative coefficient. Each coefficient is applied within the 95% confidence interval of the calculated coefficient value from the survival analysis, and preferably the point estimate of each coefficient derived from the cross validation is used.

| Coefficient | Point estimate | 95% confidence interval |
|---|---|---|
| a (MMP11) | 0.45 | 0.15~0.76 |
| b (CD2) | −0.48 | −0.81~−0.15 |

In the equation of risk score, the value standardized in the step (c) is substituted for $\Delta C_{1\_}\text{MMP11}$ or $\Delta C_{q\_}\text{CD2}$.

(e) Predicting that the Greater the Score Calculated in the Step (c) is, the Poorer the Prognosis is:

According to one example of the present invention, in the method of predicting the prognosis of breast cancer according to the present invention, the point at which the sum of the sensitivity and the specificity as parameters for evaluating the accuracy of the risk group classification was maximized was calculated. As a result, we determined that when the numerical value calculated according to the above <Equation 2> exceeded 0.53, the prognosis of breast cancer was poor (high risk of metastasis), and when the value is −0.53 or less, the prognosis of breast cancer (low risk of metastasis) was good.

In the present invention, the "sensitivity" refers to the percentage of high-risk patients in the test results of patients who have metastasized, and the 'specificity' refers to the percentage of low risk patients in the test results of patients who do not have metastasized.

In one example of the present invention, patients with HER2 subtypes were divided into two groups in order to evaluate the significance of the prognostic prediction model of the present invention. That is, according to the risk score developed in the present invention, breast cancer patients were classified into high risk group and low risk group. Aa a result of comparison of the probability of distant metastasis-free in both groups, the probability of survival of distant metastasis at 10 years after breast-removing surgery was 56.07% in the high-risk group (P-value <0.001) compared with 87.70% in the low-risk group. That is, according to the prognostic prediction model of the present invention, the probability of distant metastasis within 10 years in the high-risk group was 44.93%, which is significantly higher than 12.30% in the low-risk group. On the other hand, there was no significant difference in the clinical characteristics between the high-risk group and the low-risk group. Therefore, clinical parameter's alone were not able to distinguish high-risk or low-risk distant metastasis from HER2 subtype breast cancer patients, but the prognostic prediction model according to the present invention is very useful in distinguishing patients from high-risk and low-risk patients for distant metastasis.

In another example of the present invention, the risk score of the present invention was compared with the prognostic predictability of conventional clinicopathologic factors using Harrell's c-index. The prognostic prediction model of the present invention was found to be excellent in predicting the risk of distant metastasis due to the significantly higher c-index value compared to other prognostic prediction factors or models based only on clinicopathologic factors.

Thus, the prognostic prediction model of breast cancer according to the above Equation 1 and Equation 2 of the present invention is calculated by analyzing genes for predicting prognosis selected by analyzing a wide range of clinical samples, and related clinical information. Therefore, the predictive possibility of prognosis is significantly superior to other models such as models based on conventional clinical information. Furthermore, the prognostic prediction model of the present invention can be very useful in predicting the prognosis of HER2 type breast cancer when molecular subtypes of breast cancer are classified and applied.

The present invention also provides a composition for predicting the prognosis of a breast cancer patient, the composition comprising agents for measuring the expression levels of MMP11 and CD2 genes, respectively.

The composition may further comprise agents for measuring the expression levels of the CTBP1, CUL1 and UBQLN1 genes.

Also, another embodiment according to an aspect of the present invention provides a composition for predicting the prognosis of a breast cancer patient, the composition consisting of agents for measuring the expression level of MMP11 and CD2 genes, respectively.

Also, another embodiment according to an aspect of the present invention provides a composition for predicting the prognosis of a breast cancer patient, which is essentially consisting of agents for measuring the expression levels of MMP11 and CD2 genes, respectively.

In the present invention, the agents for measuring the expression levels of the genes may be a set of primer pair specifically binding to MMP11 and CD2 genes.

As used herein, the term "primer" refers to an oligonucleotide which acts as a starting point for synthesis at conditions under which the synthesis of a primer extension product complementary to the nucleic acid chain (template) is induced, that is, a presence of polymerases such as a nucleotide and a DNA polymerase, and suitable temperature and pH. Preferably, the primer is a deoxyribonucleotide and a single strand. The primers used in the present invention may comprise naturally occurring dNMPs (i.e., dAMP, dGMP, dCMP and dTMP), modified nucleotides or non-natural nucleotides. The primers may also include ribonucleotides.

The primer of the present invention may be an extension primer that is annealed to a target nucleic acid and forms a sequence complementary to the target nucleic acid by a template-dependent nucleic acid polymerase. It extends to a position where the immobilization probe is annealed and occupies the area where it is annealed.

The extension primer used in the present invention comprises a hybridization nucleotide sequence complementary to the first position of the target nucleic acid. The term "complementary" means that the primer or probe is sufficiently complementary to hybridize selectively to the target nucleic acid sequence under certain annealing or hybridization conditions, and is substantially complementary and perfectly complementary, and preferably means completely complementary. As used herein, the term "substantially complementary sequence" used in relation to a primer sequence is meant to include not only a completely matched sequence but also a sequence partially inconsistent with the sequence to be compared within a range that can anneal to a specific sequence and serve as a primer.

The primer should be long enough to priming the synthesis of the extension product in the presence of polymerases. The suitable length of the primer is determined by a number of factors, such as the temperature, the application, and the source of the primer, but is typically 15-30 nucleotides. Short primer molecules generally require lower temperatures to form a sufficiently stable hybrid complex with the template. The term "annealing" or "priming" means that the oligodeoxynucleotide or hexane has apposition to the template nucleic acid, and the opposition allows the polymerase to polymerize the nucleotides to form complementary nucleic acid molecules in the template nucleic acid or a portion thereof.

The sequence of the primer does not need to have a sequence completely complementary to a partial sequence of the template, and it is sufficient if the primer has sufficient complementarity within a range that hybridizes with the template and can perform the primer-specific action. Therefore, the primer in the present invention does not need to have a perfectly complementary sequence to the nucleotide sequence as a template, and it is sufficient if the primer has sufficient complementarity within a range capable of hybridizing to the gene sequence and acting as a primer. The design of such a primer can be easily carried out by those skilled in the art with reference to the nucleotide sequence described above, for example, by using a program for primer design (e.g., PRIMER 3 program).

The present invention also provides a kit for predicting the prognosis of a breast cancer patient, the kit comprising agents for measuring the expression levels of MMP11 and CD2 genes, respectively.

The kit of the present invention may further comprise tools and/or reagents known in the art for use in RNA isolation and cDNA synthesis in PCR reaction reagents, in addition to a set of primer pair capable of amplifying the MMP11 and CD2 by PCR. The kit of the present invention may further comprise a tube, a well plate to be used for mixing the respective components and an instructional material describing the method of use, if necessary.

In addition, the present invention provides the use of agents for measuring the expression levels of MMP11 and CD2 genes for preparing agents for predicting the prognosis of a breast cancer patient.

The present invention also provides the use of agents, wherein the agents for measuring the expression levels further comprises agents for measuring the expression level of CTBP1, CUL1 and UBQLN1 genes, respectively.

The "agents for measuring expression levels of the genes" of the present invention is the same as described above, the "genes for preparing agents for predicting the prognosis" is the same as described above, and is one or more selected from the group consisting of MMP11, CD2, CTBP1, CUL1 and UBQLN1.

The term "comprising" of the present invention is used synonymously with "containing" or "characterized" and does not exclude additional component elements or method steps not mentioned in the composition or method. The term "consisting of" means excluding additional elements, steps or components not otherwise mentioned. The term "essentially consisting of" refers to comprising a component element or step which is described in the range of a composition or a method and which does not substantially affect its basic.

Advantageous Effect

The present invention relates to a method for predicting the prognosis of breast cancer using the two genes showing a significant correlation with the prognosis of breast cancer. Therefore, the method of the present invention has an effect of being capable of more accurately predicting the future prognosis of metastasis, recurrence, or metastatic recurrence in breast cancer patients, and in particular, has a very excellent ability to predict the prognosis of HER2-type breast cancer, the prognosis of which is very poor, and thus can be usefully used to provide clues for the direction of future treatment of breast cancer.

MODE FOR CARRYING OUT INVENTION

Figure 1:
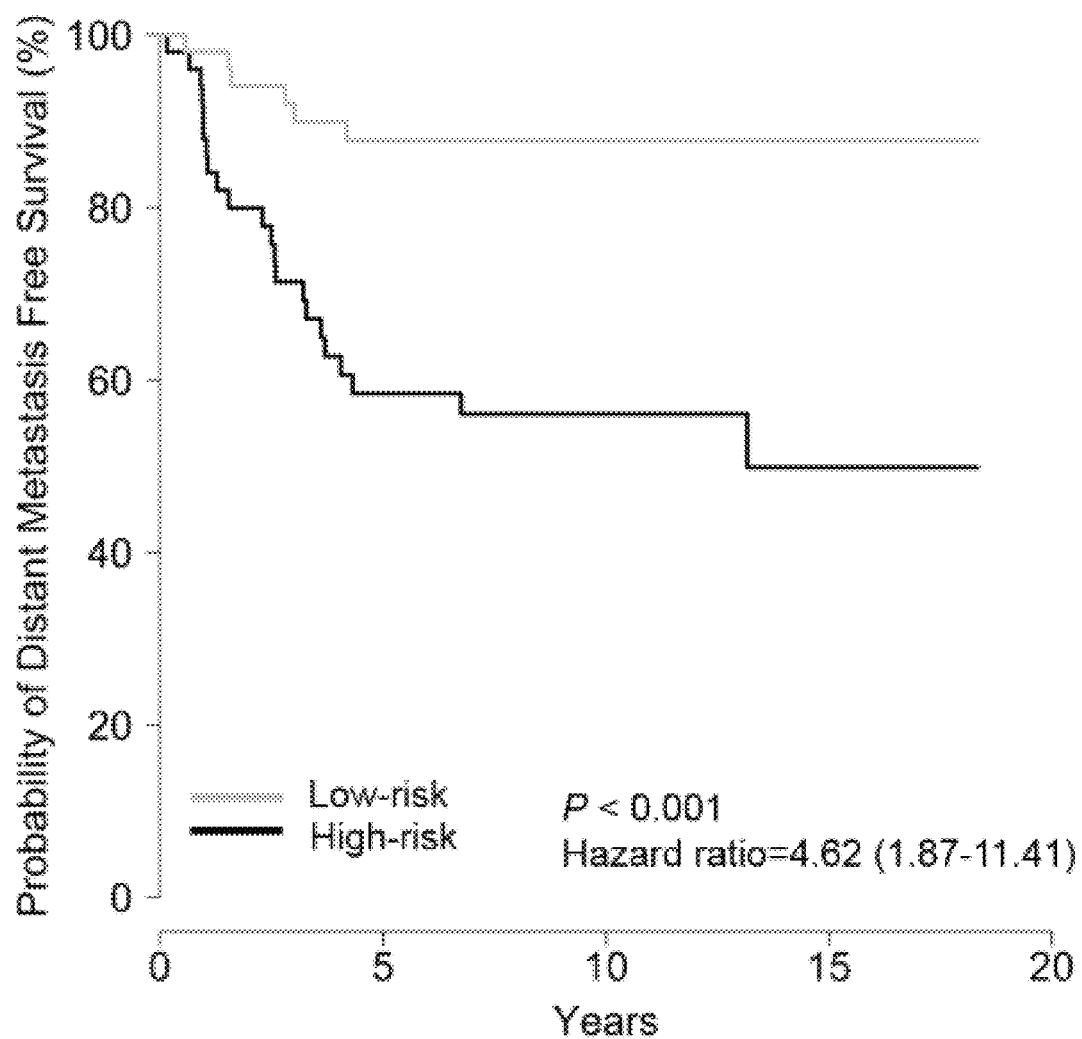
FIG. 1 is a graph showing the results of classification of HER2 subtype breast cancer patients into high-risk and low-risk groups according to the prognostic prediction model in the present invention, followed by a Kaplan-Meier plot of distant metastasis-free survival (DMFS).

Hereinafter, the present invention will be described in detail.

However, the following examples are illustrative of the present invention, and the present invention is not limited to the following examples.

<Method>

1. Biological Sample

From January 1995 to December 2002, 997 FFPE tissue specimens of breast cancer patients who underwent tumor resection with lymph node were obtained. Patients with first to third stage tumor were treated with radiation therapy, chemotherapy, or hormone therapy alone or in combination after receiving a mastectomy or breast conserving surgery. Fifty frozen tissue samples were also obtained from the same patient from which the FFPE sample was obtained. Samples with signs of inflammation, samples containing 50% fat, or samples with less than 30% of ducts and lobules were not used in the experiments. The medical records of each patient were reviewed to identify clinicopathological information including patient age, tumor size, lymph node status, pathologic stage, type of treatment and outcome of treatment. Molecular subtypes of breast cancer were classified as Luminal A (ER+ or PR+/HER2−), Luminal B (ER+ or PR+/HER2+) and HER2 (ER−/PR−/HER2+).

2. Selection of Candidate Genes for Predicting the Prognosis

In a previous study, the present inventors selected 384 genes related to the prognosis of early breast cancer patients using published gene expression microarray data (Breast cancer research and treatment 132 (2):499-509. doi:10.1007/s10549-011-1626-8). These gene candidates were categorized largely into two groups according to their physiological function: the proliferation-related gene (p-gene) and the immune response-related gene (i-gene).

From these candidate candidates, 30 genes that meet the following criteria were primarily selected:
(1) having a high related to proliferation or immune response;
(2) having high variability between samples (large quadratic deviation);
(3) having a high average expression value.

Next, based on the results of qRT-PCR, 16 genes with high expression of these genes were selected between FFPE samples and frozen tissues. These 16 genes are composed of 10 genes related to proliferation (p-gene, AURKA, CCNB2, FOXM1, MKI67, MMP11, PTTG1, RACGAP1, RRM2, TOP2A and UBE2C) and six immune response-related gene (i-gene, BTN3A2, CCL19, CD2, CD52, HLA. DPA1, and TRBC1).

3. qRT-PCR

RNA was extracted from frozen tissue using Arcturus kit (Life technologies, Grand Island, NY, USA). RNA was also extracted from FFPE tissue samples using a Tissue preparation system (Siemens AG, Munich, Germany). qRT-PCR was performed using the LightCycler 480 system (Roche applied science) and QuantiFast Multiplex RT-PCR Kit (Qiagen Hilden, Germany). The reagents were dispensed into 384-well plates via an automatic dispenser. PCR primers and probes for qRT-PCR are shown in Table 2 below.

TABLE 2

| | Gene Abbreviation | Gene description | Forward Primer Sequence Reverse Primer Sequence | Probe |
|---|---|---|---|---|
| 1 | AURKA | Aurora kinase A | CAGGGCTGCCATATAACCTGAC (SEQ ID NO: 1) CACCTGCTGAGTAAAACAAAT (SEQ ID NO: 2) | GCTGCCCT (SEQ ID NO: 39) |
| 2 | CCNB2 | Cyclin B2 | TTGGGAGAACCCTCAGCTCT (SEQ ID NO: 3) GTTTATGGACTGCAAAACCT (SEQ ID NO: 4) | CTCAGGCA (SEQ ID NO: 40) |
| 3 | FOXM1 | Forkhead box M1 | AAGCACATTGCCAAGCCAGGC (SEQ ID NO: 5) CAGGGAAAGGTTGTGGCGG (SEQ ID NO: 6) | AGGCTGGA (SEQ ID NO: 41) |
| 4 | MKI67 | Antigen identified by monoclonal antibody Ki-67 | CAGAATGAGAGCTCCCAGCCT (SEQ ID NO: 7) TGCATGAGAACCTTCGCACTC (SEQ ID NO: 8) | GAGGAGAG (SEQ ID NO: 42) |
| 5 | MMP11 | Matrix metallopeptidase 11 (stromelysin 3) | GACAGAAGAGGTTCGTGCTT (SEQ ID NO: 9) AACTGCCATGGGAACCGA (SEQ ID NO: 10) | CGCTGGGA (SEQ ID NO: 43) |
| 6 | PTTG1 | Pituitary tumor-transforming 1 | CAGGCACCCGTGTGGTTGC (SEQ ID NO: 11) ATCTAAGGCTTTGATTGAAGG (SEQ ID NO: 12) | CTGAAGCT (SEQ ID NO: 44) |
| 7 | RACGAP1 | Rac GTPase activating protein 1 pseudogene | GCTGCCATGTACCAAGCTGT (SEQ ID NO: 13) TCTCTGCAAGTGAATCATGAG (SEQ ID NO: 14) | GCCCCAGG (SEQ ID NO: 45) |
| 8 | RRM2 | Ribonucleotide reductase M2 | TGGGAATCCCTGAAACCC (SEQ ID NO: 15) GAACTTCTTGGCTAAATCGC (SEQ ID NO: 16) | AAAGCCA (SEQ ID NO: 46) |
| 9 | TOP2A | Topoisomerase (DNA) II alpha 170 kDa | AAGAGTCATTCCACGAATAACCAT (SEQ ID NO: 17) GAGGGCTTCCTTCAGTATTT (SEQ ID NO: 18) | GCCTCTGA (SEQ ID NO: 47) |
| 10 | UBE2C | Ubiquitin-conjugating enzyme E2C | AAAAGGCTACAGCAGGAGC (SEQ ID NO: 19) AGCTGCTCCATGGATGGTC (SEQ ID NO: 20) | GGGAAGGC (SEQ ID NO: 48) |

TABLE 2-continued

| Gene Abbreviation | Gene description | Forward Primer Sequence Reverse Primer Sequence | Probe |
|---|---|---|---|
| Immune-related genes | | | |
| 1 BTN3A2 | Butyrophilin subfamily 3 member A2 | CTTCAAGCCTGGTGAGGA (SEQ ID NO: 21) TTTTCTGCAGTCTATTTTTCC (SEQ ID NO: 22) | CAAGGTGG (SEQ ID NO: 49) |
| 2 CCL19 | Chemokine (C-C motif) ligand 19 | ACTTCCACTACCTTCTCATCAAG (SEQ ID NO: 23) GGCGGCCCCTCAGTGTGGT (SEQ ID NO: 24) | GTGCCTGC (SEQ ID NO: 50) |
| 3 CD2 | CD2 molecule | ACTGCTCGTTTTCTATATCA (SEQ ID NO: 25) TCCAGCTCCTCATCATTTCT (SEQ ID NO: 26) | GAGGAGTC (SEQ ID NO: 51) |
| 4 CD52 | CD52 molecule | TCCTCCTACTCACCATCAGCCT (SEQ ID NO: 27) TCGTTTTGTCCTGAGAGTCC (SEQ ID NO: 28) | TCCTGGTT (SEQ ID NO: 52) |
| 5 HLA-DPA1 | Major histocompatibility complex, class II, DP alpha 1 | GGACCCTGTGAAATACTGTAAAG (SEQ ID NO: 29) CAGCTGGAGTTCAGATCTCT (SEQ ID NO: 30) | ACAGAAGAG (SEQ ID NO: 53) |
| 6 TRBC1 | T cell receptor beta constant 1 | CAGCAAGGGGTCCTGTCTG (SEQ ID NO: 31) AAGAGAAAGGATTTCTGAAGG (SEQ ID NO: 32) | TGGCAGACA (SEQ ID NO: 54) |
| Reference genes | | | |
| 1 CTBP1 | C-terminal binding protein 1 | CCTTGGGCATCATCGGA (SEQ ID NO: 33) GTTGAAGCCGAAGGCCTT (SEQ ID NO: 34) | GCCCCACG (SEQ ID NO: 55) |
| 2 CUL1 | Cullin 1 | AGTACTGAATTCTTGCAGCAGA (SEQ ID NO: 35) TCTTCGTTGTTCCTCAAGCAGAC (SEQ ID NO: 36) | GCAGAGGC (SEQ ID NO: 56) |
| 3 UBQLN1 | Ubiquilin 1 | GAAATCCTCAGCTTCAAGAACA (SEQ ID NO: 37) TGACATTGCTGATAGTGTATCA (SEQ ID NO: 38) | TTGGGAGC (SEQ ID NO: 57) |

4. Normalization of qRT-PCR Data

The expression levels of the five reference genes were also evaluated to select the reference genes suitable for normalizing the qRT-PCR data of the 16 candidate genes. The reference genes include three new reference genes (UBQLN1, CUL1 and CTBP1) and two conventional reference genes (TBP and HMBS).

First, the expression levels of the above 5 reference genes and 16 candidate genes for predicting the prognosis were evaluated by using qRT-PCR from FFPE samples and frozen samples. Three genes (CTBP, CUL1, and UBQLN1) among the five reference genes showed relatively similar expression levels to those of 16 candidate genes for predicting the prognosis and showed excellent correlation with frozen samples and FFPE samples.

When evaluated in 926 FFPE samples, these genes exhibited relatively low loss of Cq value (CTBP1: 25 loss of value, CUL1: 89 loss of value, UBQLN1: 15 loss of value) compared to the other two genes. In addition, these genes showed high mutual correlation in gene expression as shown in Table 2 (Pearson's coefficient>0.79).

TABLE 3

The correlation among the five reference genes in the FFPE samples.

| | CTBP1 | CUL1 | HMBS | TBP | UBQLN1 |
|---|---|---|---|---|---|
| CTBR1 | 1 | 0.793 | 0.75 | 0.595 | 0.834 |
| CUL1 | | 1 | 0.684 | 0.525 | 0.782 |
| HMBS | | | 1 | 0.619 | 0.763 |
| THP | | | | 1 | 0.629 |
| UBQLN1 | | | | | 1 |

* Correlation of gene expression was analyzed by using Pearson linear correlation In addition, CTBP1, CUL1 and UBQLN1 were evaluated as the most stable genes in the analysis using the geNorm and NormFinder algorithms in R package NormqPCR (Table 4). Therefore, the three genes were selected as the reference genes in the 16 candidate genes for predicting the prognosis.

TABLE 4

Stability ranking of candidate reference genes calculated by geNorm and NormFinder

| 926 samples, missing = 41 | | 615 samples* | |
|---|---|---|---|
| geNorm | NormFinder | geNorm | NormFinder |
| CTBP1 and UBQLN1 | UBQLN1 | CTBP1 and CUL1 | HMBS |
|  | CTBP1 |  | TBP |
| CUL1 | CUL1 | UBQLN1 | CUL1 |
| HMBS | TBP | HMBS | UBQLN1 |
| TBP | HMBS | TBP | CTBP1 |

*615 samples remained after removing samples with at least one missing value in candidate reference genes The Cq value of each gene represents the relative expression value normalized by the expression levels of the three reference genes. The relative expression values of each gene are calculated based on the difference between the average Cq values of the three reference genes and the target Cq value in each sample.

$$\Delta C_q\_target = ((C_q\_CTBP1 + C_q\_CUL1 + C_q\_UBQLN1)/3) - C_q\_target + 30$$

5. Univariate and Multivariate Analysis

Clinicopathological characteristics of test specimens were summarized using descriptive statistics. Distant metastasis-free survival (DMFS) is defined as the time from the day of primary tumor surgery to the day of distant metastasis. Overall survival (OS) is defined as the period from the day of primary tumor surgery to the time of death or the time of the last visit. Disease-free survival (DFS) calculates the duration from the day of primary tumor surgery to the day of recurrence (including local recurrence and primary metastasis or all-cause mortality).

The correlation of clinicopathologic factors or gene expression with clinical outcome was assessed using hazard ratios (HRs) derived from a Cox proportional hazards model with 95% confidence intervals (CIs).

The Cq value of the missing part was analyzed by replacing the missing value using the method for qRT-PCR missing value (Bioinformatics (2014) 30 (16): 2310-2316, 2014 doi:10.109 3/bioinformatics/btu239). The distant metastatic potential was assessed by the Kaplan-Meier method and the log-rank test confirmed the significance of the difference in the probability of DMFS. P values <0.05 were considered statistically significant. All statistical analyzes were performed using R 3.2.0 (http://r-project.org).

6. Development of a Prognostic Prediction Model Using Clinical and Molecular Data Based on the results of multivariate analysis, a prognostic prediction model was developed to predict the risk of distant metastasis in the HER2 subtype. The risk score (the Molecular predictive variables of the occurrence of distant metastasis within 10 years) was calculated by the relative expression levels of two prognostic prediction genes that were normalized by the average level of expression of the three reference genes. The coefficients in each variable were taken from the Cox model and the risk score was defined as a linear combination of coefficients to predict distant metastasis according to the following equation:

$$\text{Risk score} = 0.45 \times \Delta C_q\_MMP11 - 0.48 \times \Delta C_q\_CD2$$

A high risk score means a high risk of distant metastasis. The threshold value of risk score for distinguishing between patients having high risk of distant metastasis and patients having low risk of distant metastasis is 0.53, which is the maximum sum of sensitivity and specificity. If a patient's sample has a risk score of 0.53 or greater, the patient is considered to be at high-risk group, otherwise it may be considered low-risk group.

7. Comparison of the Prognostic Prediction Model with Conventional Clinicopathologic Factors The Nottingham prognostic index (NPI) score was used to calculate the risk for distant metastasis based on clinicopathologic factors alone. NPI scores were calculated as follows:

0.2×tumor size (cm) + tumor grade + lymph node status

The NPI prognostic prediction value of each of the samples used in the present invention was calculated and divided into four groups:

2 to 2.4: Very good, 2.4 to 3.4: Good, 3.4 to 5.4: Fair, 5.4 or more: Poor

*The Harrell's concordance index (c-index) was calculated to compare the predictive possibility of prognosis and to assess the ability of each prognostic prediction model.

<Experimental Results>

1. Characteristics of Patient

Out of 997 tissue samples, samples that were histologically inadequate or have insufficient quantities were excluded from RNA extraction, and samples lacking the extracted RNA were also excluded from the qRT-PCR analysis. qRT-PCR was performed to analyze gene expression in a total of 926 FFPE samples. Of the 926 samples, samples with insufficient qRT-PCR results were excluded once more and a total of 819 breast cancer patient samples were used in this study.

The mean age of the patients was 47.3 years (ranging from 23.8 to 81.2 years) and the average size of tumor was 2.8 cm. 51.6% (423/819) patients were lymph node negative, while 396 patient samples were lymph node positive. Lymph node negative refers to the absence of tumor in the axillary lymph node, and lymph node positive means that the axillary lymph node contains the tumor. 86.3% (707/819) patients received chemotherapy treatment. Detailed information on the clinicopathologic characteristics of breast cancer patients according to molecular subtypes is shown in Table 5 below.

TABLE 5

| | Total (n = 819) n (%) | Luminal A (n = 410) n (%) | Luminal B (n = 112) n (%) | HER2 (n = 105) n (%) | TNBC (n = 192) n (%) |
|---|---|---|---|---|---|
| Median age (min-max) Age (years) | 47.3 (23.8-81.2) | 47.3 (25.2-80.5) | 45.5 (26.0-77.4) | 52.8 (24.3-77.8) | 46 (23.8-81.2) |
| <50 | 486 (59.3%) | 241 (58.8%) | 76 (67.9%) | 43 (41.0%) | 126 (65.6%) |
| >=50 | 333 (40.7%) | 169 (41.2%) | 36 (32.1%) | 62 (59.0%) | 66 (34.4%) |

TABLE 5-continued

|  | Total (n = 819) n (%) | Luminal A (n = 410) n (%) | Luminal B (n = 112) n (%) | HER2 (n = 105) n (%) | TNBC (n = 192) n (%) |
|---|---|---|---|---|---|
| Tumor size (cm) | | | | | |
| <=2 | 325 (39.7%) | 183 (44.6%) | 39 (34.8%) | 32 (30.5%) | 71 (37.0%) |
| 2-5 | 438 (53.5%) | 204 (49.8%) | 65 (58.0%) | 63 (60.0%) | 106 (55.2%) |
| >5 | 56 (6.8%) | 23 (5.6%) | 8 (7.1%) | 10 (9.5%) | 15 (7.8%) |
| Lymph node | | | | | |
| Negative | 423 (51.6%) | 203 (49.5%) | 45 (40.2%) | 59 (56.2%) | 116 (60.4%) |
| Positive | 396 (48.4%) | 207 (50.5%) | 67 (59.8%) | 46 (43.8%) | 76 (39.6%) |
| pN | | | | | |
| 0 | 423 (51.7%) | 203 (49.5%) | 45 (40.2%) | 59 (56.2%) | 116 (60.4%) |
| 1 | 214 (26.1%) | 112 (27.3%) | 40 (35.7%) | 22 (21.0%) | 40 (20.8%) |
| 2 | 97 (11.8%) | 51 (12.4%) | 16 (14.3%) | 11 (10.5%) | 19 (9.9%) |
| 3 | 85 (10.4%) | 44 (10.7%) | 11 (9.8%) | 13 (12.4%) | 17 (8.9%) |
| Pathologic Stage | | | | | |
| I | 204 (24.9%) | 113 (27.6%) | 17 (15.2%) | 20 (19.0%) | 54 (28.1%) |
| II | 417 (50.9%) | 197 (48.0%) | 64 (57.1%) | 58 (55.2%) | 98 (51.0%) |
| III | 198 (24.2%) | 100 (24.4%) | 31 (27.7%) | 27 (25.7%) | 40 (20.8%) |
| Histologic Grade | | | | | |
| 1 | 93 (11.4%) | 77 (18.8%) | 8 (7.1%) | 4 (3.8%) | 4 (2.1%) |
| 2 | 300 (36.6%) | 199 (48.5%) | 37 (33.0%) | 24 (22.9%) | 40 (20.8%) |
| 3 | 366 (44.7%) | 123 (30%) | 59 (52.7%) | 66 (62.9%) | 118 (61.5%) |
| Unknown | 60 (7.3%) | 11 (2.7%) | 8 (7.1%) | 11 (10.5%) | 30 (15.6%) |
| Nuclear Grade | | | | | |
| 1 | 81 (9.9%) | 60 (14.6%) | 7 (6.3%) | 2 (1.9%) | 12 (6.3%) |
| 2 | 402 (49.1%) | 256 (62.4%) | 55 (49.1%) | 35 (33.3%) | 56 (29.2%) |
| 3 | 307 (37.5%) | 81 (19.8%) | 46 (41.1%) | 65 (61.9%) | 115 (59.9%) |
| Unknown | 29 (3.5%) | 13 (3.2%) | 4 (3.6%) | 3 (2.9%) | 9 (4.7%) |
| Hormone therapy | | | | | |
| No | 301 (36.8%) | 21 (5.1%) | 11 (9.8%) | 96 (91.4%) | 173 (90.1%) |
| Yes | 508 (62.0%) | 379 (92.4%) | 101 (90.2%) | 9 (8.6%) | 19 (9.9%) |
| Unknown | 10 (1.2%) | 10 (2.4%) | 0 (0.0%) | 0 (0.0%) | 0 (0.0%) |
| Chemotherapy | | | | | |
| No | 110 (13.4%) | 68 (16.6%) | 14 (12.5%) | 14 (13.3%) | 14 (7.3%) |
| Yes | 707 (86.3%) | 342 (83.4%) | 97 (86.6%) | 90 (85.7%) | 178 (92.7%) |
| Unknown | 2 (0.3%) | 0 (0.0%) | 1 (0.9%) | 1 (1.0%) | 0 (0.0%) |
| Radiotherapy | | | | | |
| No | 352 (43.0%) | 162 (39.5%) | 50 (44.6%) | 59 (56.2%) | 81 (42.2%) |
| Yes | 465 (56.8%) | 247 (60.2%) | 61 (54.5%) | 46 (43.8%) | 111 (57.8%) |
| Unknown | 2 (0.2%) | 1 (0.2%) | 1 (0.9%) | 0 (0.0%) | 0 (0.0%) |

Abbreviations:
HER2, human epidermal growth factor receptor 2;
TNBC, triple-negative breast cancer;
pT, pathologic tumor size;
pN, pathologic noda status The majority of the 819 samples were subtypes of hormone receptor positive (HR+) such as Luminal A type (50%) and Luminal B type (13.7%). HER2 type was 12.8% and triple negative breast cancer (TNBC) was 23.4%. Luminal A type had more histological grade 1 and 2, whereas HER2 type and triple negative breast cancer had more grade 3 histological grade. The median age of HER2 type was 52.8 years (range, 24.3~77.8) and the other breast cancer subtype was the median age of 46.0 to 47.3 years. Thus, it was shown that HER2 type was found in older people. And the size of cancer according to molecular subtype of breast cancer had similar distribution to each other.

2. Multivariate Analysis According to Molecular Subtype

The Kaplan-Meier analysis was performed to analyze the correlation of breast cancer subtypes and patient survival including survival, disease-free survival, and overall survival. The maximum period of the observation was 19.46 years after surgery. HER2 type (HR-/HER2+) tended to show a worse prognosis than other subtypes during this period, but it was not statistically significant. However, a statistically similar difference was found between HER2 type and other subtypes in overall survival (OS) and disease free survival (DFS) when the 5-year period was limited. Luminal A (HR+/HER2-) type had the best prognosis, followed by Luminal B (HR+/HER2+) type, triple negative breast cancer (TNBC) and finally HER2 type.

The present inventors analyzed the correlation on the expression of 16 gene candidates, conventional clinico-pathologic factors, and clinical outcome according to the molecular subtypes of breast cancer. The average period of observation for distant metastasis-free survival (DMFS) was 9.67 years (range 0.04 to 19.46 years). The rates of DMFS at 5, 10 and 15 years were 79.3%, 74.3% and 70.0%, respectively.

Univariate analysis showed that lymph node positivity was associated with high risk of distant metastasis regardless of the subtype of breast cancer except the HER2 subtype of breast cancer (Table 6 and Table 7).

TABLE 6

Multivariate analysis for DMFS of clinical variables according to breast cancer subtype

| | Total | | | Luminal A | | |
|---|---|---|---|---|---|---|
| | HR | 95% CI | P value | HR | 95% CI | P value |
| Years | | | | | | |
| <50 | 1.00 | | | 1.00 | | |
| ≥50 | 0.74 | 0.56 0.99 | 0.042 | 0.76 | 0.51 1.14 | 0.184 |

TABLE 6-continued

Multivariate analysis for DMFS of clinical variables according to breast cancer subtype

| | Total | | | Luminal A | | |
|---|---|---|---|---|---|---|
| | HR | 95% CI | P value | HR | 95% CI | P value |
| Tumor size (cm) | | | | | | |
| ≤2 | 1.00 | | | 1.00 | | |
| 2-5 | 1.70 | 1.25 2.30 | 0.001 | 1.59 | 1.06 2.40 | 0.025 |
| >5 | 2.13 | 1.26 3.60 | 0.005 | 2.25 | 1.08 4.66 | 0.029 |
| Lymph node metastasis | | | | | | |
| Negative | 1.00 | | | 1.00 | | |
| Positive | 2.74 | 2.04 3.68 | <0.001 | 3.04 | 1.99 4.66 | <0.001 |
| Histological grade | | | | | | |
| 1 | 1.00 | | | 1.00 | | |
| 2 | 1.64 | 0.90 2.97 | 0.104 | 1.56 | 0.83 2.94 | 0.169 |
| 3 | 2.40 | 1.35 4.26 | 0.003 | 2.33 | 1.22 4.44 | 0.010 |

TABLE 7

Multivariate analysis for DMFS of clinical variables according to breast cancer subtype

| | Luminal B | | | HER2 | | | TNBC | | |
|---|---|---|---|---|---|---|---|---|---|
| | HR | 95% CI | P value | HR | 95% CI | P value | HR | 95% CI | P value |
| Years | | | | | | | | | |
| <50 | 1.00 | | | 1.00 | | | 1.00 | | |
| ≥50 | 0.47 | 0.19 1.15 | 0.098 | 0.83 | 0.39 1.76 | 0.630 | 0.76 | 0.39 1.50 | 0.431 |
| Tumor size (cm) | | | | | | | | | |
| ≤2 | 1.00 | | | 1.00 | | | 1.00 | | |
| 2-5 | 1.13 | 0.53 2.43 | 0.745 | 2.39 | 0.90 6.35 | 0.081 | 2.18 | 1.02 4.63 | 0.044 |
| >5 | 1.05 | 0.23 4.82 | 0.947 | 1.68 | 0.32 8.64 | 0.538 | 3.91 | 1.31 11.68 | 0.015 |
| Lymph node metastasis | | | | | | | | | |
| Negative | 1.00 | | | 1.00 | | | 1.00 | | |
| Positive | 2.78 | 1.20 6.42 | 0.017 | 1.87 | 0.88 3.96 | 0.101 | 2.82 | 1.51 5.29 | 0.001 |
| Histological grade | | | | | | | | | |
| 1 | 1.00 | | | — | | | — | | |
| 2 | 1.13 | 0.13 9.64 | 0.914 | 1.00 | | | 1.00 | | |
| 3 | 3.89 | 0.52 28.90 | 0.184 | 1.05 | 0.41 2.65 | 0.925 | 1.36 | 0.59 3.14 | 0.468 |

Interestingly, it was confirmed that the effect of tumor size on the risk of distant metastasis was significant in HER2-negative breast cancer (Luminal A, TNBC subtype) including Luminal A and TNBC subtypes, but not significant for HER2 positive breast cancer (Luminal B, HER2 subtype).

The correlation of 16 gene expression with distant metastasis was dependent on the molecular subtypes of breast cancer. Of the 16 genes for predicting the prognosis, most proliferation-related genes were significantly related to DMFS in Luminal A type of breast cancer. The high expression of nine proliferation-associated genes (AURKA, CCNB2, FOXM1, MK167, MMP11, RACGAP1, RRM2, TOP2A and UBE2C) showed a significant association with the high risk of distant metastasis in the subtypes (Table 8 and Table 9).

TABLE 8

Multivariate analysis for DMFS of clinical variables according to breast cancer subtype

| | Total | | | | HR+/HER2− | | | |
|---|---|---|---|---|---|---|---|---|
| | HR | 95% CI | | P value | HR | 95% CI | | P value |
| Proliferation-related genes | | | | | | | | |
| AURKA | 1.07 | 0.99 | 1.15 | 0.086 | 1.16 | 1.04 | 1.29 | 0.006 |
| CCNB2 | 1.12 | 0.98 | 1.28 | 0.096 | 1.32 | 1.09 | 1.60 | 0.005 |
| FOXM1 | 1.17 | 1.03 | 1.33 | 0.015 | 1.37 | 1.14 | 1.65 | 0.001 |
| MKI67 | 1.19 | 1.03 | 1.38 | 0.017 | 1.36 | 1.11 | 1.66 | 0.002 |
| MMP11 | 1.27 | 1.15 | 1.40 | <0.001 | 1.22 | 1.06 | 1.39 | 0.004 |
| PTTG1 | 1.02 | 0.85 | 1.21 | 0.853 | 1.02 | 0.79 | 1.32 | 0.896 |
| RACGAP1 | 1.14 | 0.99 | 1.32 | 0.078 | 1.24 | 1.02 | 1.51 | 0.028 |
| RRM2 | 1.17 | 1.02 | 1.35 | 0.026 | 1.40 | 1.14 | 1.71 | 0.001 |
| TOP2A | 1.19 | 1.09 | 1.31 | <0.001 | 1.38 | 1.21 | 1.56 | <0.001 |
| UBE2C | 1.23 | 1.09 | 1.39 | 0.001 | 1.44 | 1.21 | 1.71 | <0.001 |
| Immune response-related genes | | | | | | | | |
| BTN3A2 | 0.90 | 0.77 | 1.06 | 0.208 | 0.87 | 0.69 | 1.09 | 0.220 |
| CCL19 | 0.98 | 0.89 | 1.09 | 0.730 | 0.99 | 0.86 | 1.14 | 0.860 |
| CD2 | 0.96 | 0.86 | 1.07 | 0.445 | 1.03 | 0.89 | 1.20 | 0.687 |
| CD52 | 0.99 | 0.97 | 1.01 | 0.177 | 0.99 | 0.96 | 1.02 | 0.651 |
| HLADPA1 | 1.00 | 0.89 | 1.12 | 0.973 | 0.95 | 0.81 | 1.11 | 0.502 |
| TRBC1 | 0.93 | 0.79 | 1.09 | 0.356 | 0.91 | 0.72 | 1.15 | 0.439 |

TABLE 9

Multivariate analysis for DMFS of clinical variables according to breast cancer subtype

| | HR+/HER2+ | | | | HR−/HER2+ | | | | TNBC | | | |
|---|---|---|---|---|---|---|---|---|---|---|---|---|
| | HR | 95% CI | | P value | HR | 95% CI | | P value | HR | 95% CI | | P value |
| Proliferation-related genes | | | | | | | | | | | | |
| AURKA | 1.02 | 0.84 | 1.24 | 0.806 | 1.21 | 0.99 | 1.47 | 0.067 | 0.88 | 0.75 | 1.04 | 0.140 |
| CCNB2 | 1.07 | 0.76 | 1.50 | 0.710 | 0.99 | 0.64 | 1.54 | 0.976 | 0.93 | 0.64 | 1.35 | 0.697 |
| FOXM1 | 1.24 | 0.83 | 1.85 | 0.294 | 1.04 | 0.61 | 1.75 | 0.898 | 1.05 | 0.75 | 1.47 | 0.763 |
| MKI67 | 1.22 | 0.86 | 1.73 | 0.270 | 1.12 | 0.76 | 1.64 | 0.578 | 0.95 | 0.65 | 1.38 | 0.772 |
| MMP11 | 1.39 | 1.07 | 1.80 | 0.012 | 1.57 | 1.16 | 2.13 | 0.003 | 1.16 | 0.92 | 1.46 | 0.208 |
| PTTG1 | 1.25 | 0.84 | 1.86 | 0.267 | 0.97 | 0.57 | 1.66 | 0.917 | 0.93 | 0.60 | 1.43 | 0.736 |
| RACGAP1 | 1.27 | 0.82 | 1.96 | 0.282 | 1.10 | 0.71 | 1.71 | 0.677 | 0.94 | 0.66 | 1.35 | 0.751 |
| RRM2 | 1.65 | 1.07 | 2.53 | 0.022 | 0.81 | 0.52 | 1.26 | 0.343 | 0.89 | 0.64 | 1.22 | 0.451 |
| TOP2A | 1.21 | 0.96 | 1.51 | 0.104 | 0.99 | 0.74 | 1.34 | 0.971 | 0.89 | 0.69 | 1.15 | 0.380 |
| UBE2C | 1.43 | 1.01 | 2.04 | 0.046 | 0.69 | 0.45 | 1.07 | 0.096 | 1.17 | 0.88 | 1.55 | 0.277 |
| Immune response-related genes | | | | | | | | | | | | |
| BTN3A2 | 1.07 | 0.68 | 1.68 | 0.772 | 0.56 | 0.35 | 0.88 | 0.013 | 1.12 | 0.81 | 1.55 | 0.484 |
| CCL19 | 0.89 | 0.68 | 1.17 | 0.403 | 0.91 | 0.70 | 1.18 | 0.465 | 1.12 | 0.89 | 1.40 | 0.345 |
| CD2 | 0.93 | 0.70 | 1.24 | 0.628 | 0.61 | 0.44 | 0.85 | 0.004 | 1.06 | 0.82 | 1.38 | 0.650 |
| CD52 | 0.98 | 0.92 | 1.04 | 0.467 | 0.97 | 0.92 | 1.02 | 0.216 | 0.99 | 0.95 | 1.03 | 0.698 |
| HLADPA1 | 0.93 | 0.69 | 1.26 | 0.658 | 0.89 | 0.68 | 1.18 | 0.426 | 1.28 | 0.98 | 1.67 | 0.075 |
| TRBC1 | 1.01 | 0.65 | 1.57 | 0.960 | 0.67 | 0.45 | 0.99 | 0.043 | 1.15 | 0.83 | 1.60 | 0.403 |

Three proliferation-related genes (MMP11, RRM2 and UBE2C) were associated with DMFS of Luminal B type of breast cancer. In the HER2 subtype, MMP11 and two immune response-related genes (BTN3A2 and CD4 were significantly associated with clinical outcome. Higher expression of MMP11 metastasis (HR, 1.57; 95% CI, 1.16-2.13; P=0.003) increased the risk of distant metastasis, whereas higher expression of BTN3A2 (HR, 0.56; 95% CI, 0.35-0.88; P=0.013) and CD2 (HR, 0.61; 95% CI, 0.44-0.85; P=0.004) was associated with better prognosis (Table 7).

Univariate analysis results for DFS and OS were similar to those of DMFS. Regarding clinical variables, lymph node metastasis was associated with DFS in all breast cancer subtypes except the HER2 subtype of breast cancer. On the other hand, the size of the tumor was significantly associated with DFS only in HER2 negative breast cancer, including Luminal A type and triple negative breast cancer. In OS, only HER2-negative breast cancer (Luminal A type and triple negative breast cancer) was associated with lymph node metastasis and cancer size. Conversely, it is no correlation between clinical parameters and OS in HER2-positive breast cancer (Luminal B type and HER2 breast cancer).

As with DMFS, genes that have a significant association with DFS or OS, were dependent on the molecular subtype of breast cancer, and the genes was similar to that of DMFS. In addition, a significant correlation between the expression of the immune response-related genes and the favorable outcome was observed only in the HER2 subtype as in DMFS. CD2 was found to be associated with DFS only in the HER2 breast cancer subtype, while BTN3A2, CD2 and TRBC2 were associated with OS in the HER2 breast cancer subtype.

In the analysis of genes associated with DFS and OS in each type according to lymph node, it was confirmed that the genes associated with lymph node status were slightly different.

3. Multivariate Analysis According to Molecular Subtype

A stepwise multivariate analysis was performed to select independent factors of predicting the prognosis for each breast cancer out of clinical and genetic parameters that were found to be significant in univariate analysis. The HR and 95% CIs for DMFS are shown in Table 10 and Table 11.

TABLE 10

Multivariate analysis of DMFS according to molecular subtype

| | Total | | | | HR+/HER2− | | | |
|---|---|---|---|---|---|---|---|---|
| | HR | 95% CI | | P value | HR | 95% CI | | P value |
| Lymph node | | | | | | | | |
| Negative | 1.00 | | | | 1.00 | | | |
| Positive | 2.74 | 2.03 | 3.68 | <0.001 | 2.95 | 1.91 | 4.56 | <0.001 |
| Proliferation-related genes | | | | | | | | |
| MKI67 | 1.13 | 0.96 | 1.32 | 0.149 | 1.25 | 0.99 | 1.58 | 0.059 |
| MMP11 | 1.22 | 1.11 | 1.35 | <0.001 | 1.12 | 0.98 | 1.29 | 0.104 |
| RRM2 | | | | | | | | |
| TOP2A | 1.16 | 1.05 | 1.28 | 0.004 | 1.26 | 1.09 | 1.44 | 0.001 |
| Immune response-related genes | | | | | | | | |
| CD2 | | | | | | | | |

TABLE 11

Multivariate analysis of DMFS according to molecular subtype

| | HR+/HER2+ | | | | HR−/HER2+ | | | | TNBC | | | |
|---|---|---|---|---|---|---|---|---|---|---|---|---|
| | HR | 95% CI | | P value | HR | 95% CI | | P value | HR | 95% CI | | P value |
| Lymph node | | | | | | | | | | | | |
| Negative | 1.00 | | | | | | | | 1.00 | | | |
| Positive | 2.75 | 1.19 | 6.38 | 0.018 | | | | | 2.82 | 1.51 | 5.29 | 0.001 |
| Proliferation-related genes | | | | | | | | | | | | |
| MKI67 | | | | | | | | | | | | |
| MMP11 | 1.32 | 1.00 | 1.73 | 0.050 | 1.49 | 1.08 | 2.04 | 0.014 | | | | |
| RRM2 | 1.48 | 0.97 | 2.28 | 0.070 | | | | | | | | |
| TOP2A | | | | | | | | | | | | |
| Immune response-related genes | | | | | | | | | | | | |
| CD2 | | | | | 0.66 | 0.47 | 0.94 | 0.022 | | | | |

As a result of univariate analysis, HER2 breast cancer, in which no significant clinicopathologic factor was found in DMFS and only prognostic genes (MMP11, BTN3A2, CD2, TRBC4 were significant. However, in multivariate analysis of HER2 breast cancer, MMP11 (HR, 1.49; 95% CI, 1.08-2.04; P=0.014) and CD2 (HR, 0.66; 95% CI, 0.47-0.94; P=0.022) were statistically significant for DMFS. These results demonstrate that the expression of MMP11 and CD2 is an independent prognostic factor in the HER2 breast cancer subtype. Lymph node metastasis was found to be an independent prognostic factor in other breast cancer subtypes except HER2 breast cancer subtype. In addition, MKI67 and TOP2A were significant factors for DMFS in Luminal A subtype, and MMP11 was found to be marginally significant in Luminal A subtype.

In DFS, MMP11 (HR, 1.46; 95% CI, 1.11-192, P=0.006) and TOP2A (HR, 0.62; 95% CI, 0.41-0.94, P=0.024) were associated with the prognosis of the HER2 subtype. MMP11 (HR, 1.47; 95% CI, 1.05-2.06, P=0.025) and BTN3A2 (HR, 0.56; 95% CI, 0.34-0.92; P=0.023) were identified as independent prognostic factors of OS in HER2 subtype.

4. Predictive Possibility of Prognosis in a Risk Model for Distant Metastasis in HER2 Subtype Breast Cancer Based on the results of multivariate analysis showing that gene expression of MMP11 and CD2 gene is an independent factor of predicting the prognosis for distant metastasis in breast cancer patients of HER2 subtype, we established a prognostic prediction model to predict the risk of distant metastasis in the HER2 subtype.

In order to evaluate the significance of the prognostic prediction model in the present invention, patients with the HER2 subtype were divided into two groups. That is, the patient group was classified into a high risk group and a low risk group using the risk score described in the above-mentioned "Experiment method 6" developed according to the prognosis prediction model in the present invention, and the DMFS probabilities of the two groups were compared.

According to the Kaplan-Meier curve, the probability of DMFS within 10 years was significantly lower in 56.07% of the high-risk group compared with 87.70% of the low-risk group, and the difference in survival probability between the two groups was significant (p <0.001, FIG. 1.). That is, the high risk group means that the rate of distant metastasis within 10 years was 44.93%, which was significantly higher than the 12.30% of low risk group. In addition, the risk ratio of the high risk group to the low risk group was derived by the Cox proportional hazards mode. As a result, HR value was 4.62(1.87-11.41), and it was shown that high-risk group had higher risk of distant metastasis than low-risk group. However, the analysis of clinical features between high-risk and low-risk groups showed no significant differences (Table 12).

TABLE 12

| | low-risk group | high-risk group | P values |
|---|---|---|---|
| Samples | 52 | 52 | |
| Age (median) | 51.6 | 51.3 | 0.883[a] |
| Tumor size (mean) | 3.01 | 3.05 | 0.909[a] |
| Tumor size | | | 0.409[b] |
| <=2 cm | 15 | 17 | |
| 2-5 cm | 30 | 32 | |
| >5 cm | 7 | 3 | |
| Chemical treatment | | | 1.000[b] |
| No | 7 | 6 | |
| Yes | 45 | 45 | |
| NA | 0 | 1 | |
| Lymph node | | | 0.844[b] |
| Negative | 30 | 28 | |
| Positive | 22 | 24 | |
| pN | | | 0.971[b] |
| 0 | 30 | 28 | |
| 1 | 11 | 11 | |
| 2 | 5 | 6 | |
| 3 | 6 | 7 | |
| Pathologic Stage | | | 0.973[b] |
| I | 10 | 10 | |
| II | 29 | 28 | |
| III | 13 | 14 | |
| Histologic Grade | | | 0.290[c] |
| 1 | 1 | 3 | |
| 2 | 10 | 13 | |
| 3 | 38 | 28 | |
| NA | 3 | 8 | |
| NPI | | | 0.342[c] |
| 1 | 2 | 5 | |
| 2 | 13 | 14 | |
| 3 | 27 | 17 | |
| 4 | 7 | 8 | |
| NA | 3 | 8 | |

[a]Student's t-test; [b]Chi-square test; [c]Fisher's exact test
Abbreviations:
NPI, Nottingham prognostic index, P values of less than 0.05 are marked in bold.

These results suggest that clinical variables alone cannot distinguish between high-risk or low-risk groups with distant metastasis in breast cancer patients with HER2 subtype, but the prognostic prediction model according to the present invention is very useful in distinguishing patients from high-risk and low-risk groups for distant metastasis.

Figure 2:
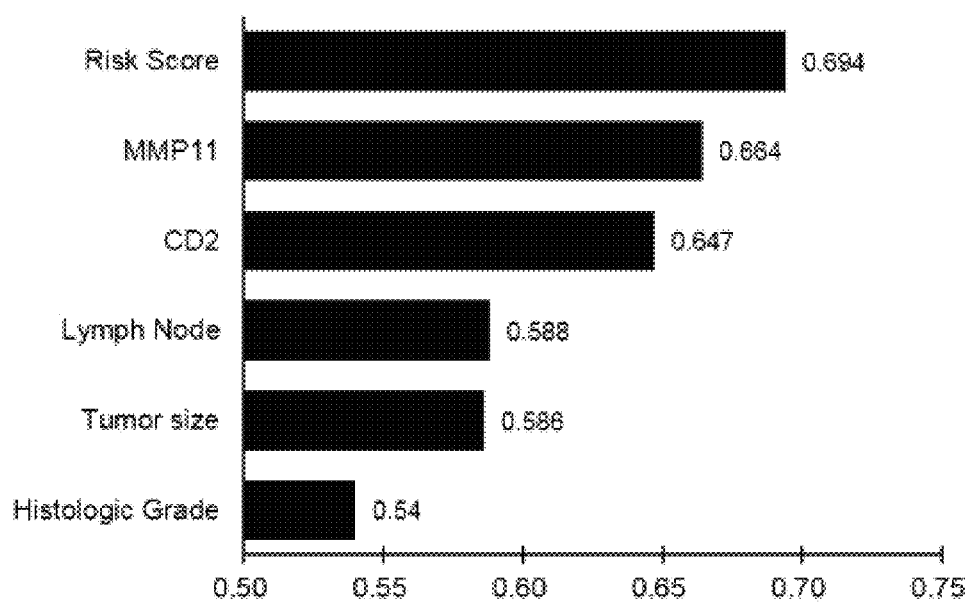
FIG. 2 shows the results of comparing the risk score according to the present invention with prognostic predictability of conventional clinicopathological factors using Harrell's c-index.
Figure 2:
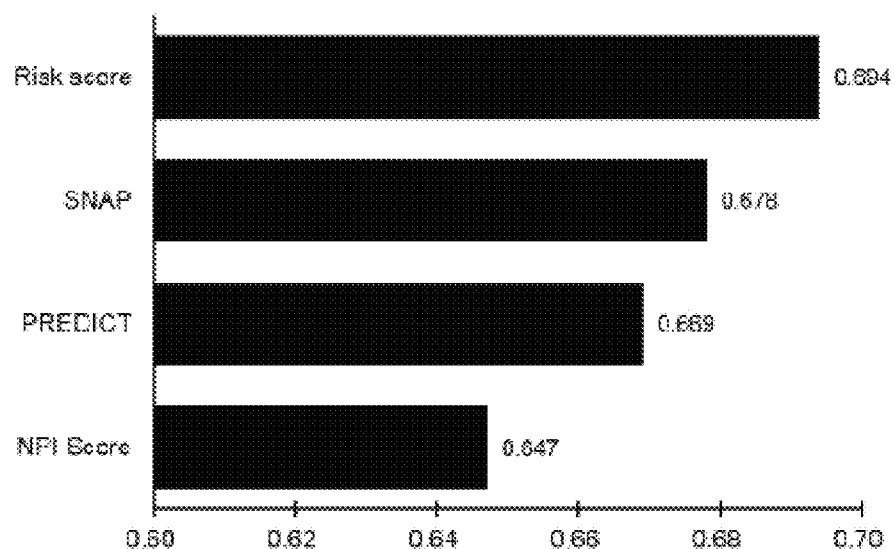

The predictive possibility of prognosis for the risk score according to the present invention and conventional clinicopathologic factors was compared using Harrell's c-index. The model according to the present invention was found to have the highest c-index of 0.694, which is superior in predicting the risk of distant metastasis compared with other prognostic prediction factors or models based only on clinicopathologic factors (FIG. 2).

As described above, the prognostic prediction model according to the present invention is superior in predicting the risk of distant metastasis compared with the conventional model based on only clinical variables, and it provides more significant information of prognostic prediction than general clinicopathologic factors.

INDUSTRIAL APPLICABILITY

The present invention relates to a method for predicting the prognosis of breast cancer using the two genes showing a significant correlation with the prognosis of breast cancer. Therefore, the method of the present invention has an effect of being capable of more accurately predicting the future prognosis of metastasis, recurrence, or metastatic recurrence in breast cancer patients, and in particular, has a very excellent ability to predict the prognosis of HER2-type breast cancer, the prognosis of which is very poor, and thus can be usefully used to provide clues for the direction of future treatment of breast cancer. Thus, it is highly industrially applicable.

What is claimed is:

1. A method for treating a human epidermal growth factor receptor (HER2) subtype breast cancer in a breast cancer patient, the method comprising the steps of:
   (a) measuring mRNA expression levels of MMP11 (matrix metallopeptidase 11) and CD2 (cluster of differentiation 2) from a breast tissue sample;
   (b) normalizing the mRNA expression levels of the genes selected and measured in the step (a) to determine a normalized value of the mRNA expression levels;
   (c) detecting an increase in a normalized value of the mRNA expression level of MMP11 compared to a reference breast tumor and a decrease in a normalized value of the mRNA expression level of CD2 compared to a reference breast tumor;
   (d) diagnosing the breast cancer patient who has an increase in a normalized value of the mRNA expression level of MMP11 compared to a reference breast tumor and a decrease in a normalized value of the mRNA expression level of CD2 compared to a reference breast tumor as requiring treatment; and
   (e) treating the diagnosed breast cancer patient by administering at least one of an anti-cancer agent, a surgery, and a radiation therapy.

2. The method of claim 1, wherein the diagnosis is the occurrence of a distant metastasis.

3. The method of claim 1, wherein the step of normalizing comprises calculating a relative expression value against an expression level of one or more selected reference genes selected from the group consisting of CTBP1 (C-terminal-binding protein 1), CUL1 (cullin 1) and UBQLN1 (Ubiquilin 4).

4. The method of claim 1, wherein the breast tissue sample is selected from the group consisting of a formalin-fixed paraffin-embedded (FFPE) tissue, a fresh tissue, and a frozen tissue containing a cancer cell of the patient.

5. The method of claim 1, wherein the expression level of the gene is measured by a method selected from the group consisting of a microarray, a polymerase chain reaction (PCR), a RT-PCR, a quantitative RT-PCR (4RT-PCR), real-time PCR, northern blot, DNA chip, and RNA chip.

\* \* \* \* \*